(12) United States Patent
Buck, Jr. et al.

(10) Patent No.: US 10,478,556 B2
(45) Date of Patent: Nov. 19, 2019

(54) PROBABILITY BASED CONTROLLER GAIN

(71) Applicant: Roche Diabetes Care, Inc., Indianapolis, IN (US)

(72) Inventors: Harvey B. Buck, Jr., Indianapolis, IN (US); David L. Duke, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 306 days.

(21) Appl. No.: 15/061,202

(22) Filed: Mar. 4, 2016

(65) Prior Publication Data
US 2017/0252513 A1   Sep. 7, 2017

(51) Int. Cl.
| | |
|---|---|
| G01N 33/48 | (2006.01) |
| A61M 5/172 | (2006.01) |
| G05B 13/02 | (2006.01) |
| G06N 7/00 | (2006.01) |
| A61B 5/00 | (2006.01) |
| A61B 5/145 | (2006.01) |

(52) U.S. Cl.
CPC ....... *A61M 5/1723* (2013.01); *A61B 5/14532* (2013.01); *A61B 5/7221* (2013.01); *G05B 13/024* (2013.01); *G06N 7/005* (2013.01); A61M 2205/3584 (2013.01); A61M 2205/3592 (2013.01); A61M 2205/52 (2013.01); A61M 2230/005 (2013.01); A61M 2230/201 (2013.01)

(58) Field of Classification Search
None
See application file for complete search history.

(56) References Cited

U.S. PATENT DOCUMENTS

| | | |
|---|---|---|
| 6,572,545 B2 | 6/2003 | Knobbe et al. |
| 6,575,905 B2 | 6/2003 | Knobbe et al. |

(Continued)

FOREIGN PATENT DOCUMENTS

| | | |
|---|---|---|
| WO | 2002/24065 A1 | 3/2002 |
| WO | 2013/032965 A1 | 3/2013 |

(Continued)

OTHER PUBLICATIONS

International Search Report dated Aug. 21, 2017, pertaining to PCT/US2017/029072, filed Apr. 24, 2017, 6 pages.

(Continued)

*Primary Examiner* — Larry D Riggs, II
(74) *Attorney, Agent, or Firm* — Dinsmore & Shohl, LLP

(57) ABSTRACT

Methods and systems are disclosed for estimating a glucose level of a person having diabetes and selecting automatically open-loop and closed-loop control for a connected therapy delivery device. The method may comprise analyzing measured glucose results and corresponding impedance values received from a glucose sensor coupled to the person with a probability analysis tool implemented by a microcontroller to determine a total quality score that is based on the minimum constraint of a probability of glucose sensor accuracy determined measured glucose results and a probability of sensing quality determined from the impedance values. The microcontroller may estimate the glucose level of the person with a recursive filter based on the plurality of measured glucose results weighted with the total quality score and select automatically either open-loop control or closed-loop control for the connected therapy delivery device based on the value of the total quality score.

44 Claims, 10 Drawing Sheets

(56) References Cited

U.S. PATENT DOCUMENTS

| | | |
|---|---|---|
| 8,843,321 B2 | 9/2014 | Duke et al. |
| 8,977,504 B2 | 3/2015 | Hovorka |
| 2002/0106709 A1 | 8/2002 | Potts et al. |
| 2004/0167464 A1 | 8/2004 | Ireland et al. |
| 2010/0262434 A1 | 10/2010 | Shaya |
| 2011/0071464 A1 | 3/2011 | Palerm |
| 2011/0184267 A1 | 7/2011 | Duke et al. |
| 2011/0257627 A1 | 10/2011 | Hovorka |
| 2011/0313674 A1 | 12/2011 | Duke et al. |
| 2014/0005505 A1 | 1/2014 | Peyser et al. |
| 2014/0066887 A1 | 3/2014 | Mastrototaro et al. |
| 2014/0100435 A1 | 4/2014 | Duke et al. |
| 2014/0187887 A1 | 7/2014 | Dunn et al. |
| 2014/0188400 A1 | 7/2014 | Dunn et al. |
| 2014/0221966 A1 | 8/2014 | Buckingham et al. |
| 2014/0235981 A1 | 8/2014 | Hayter |
| 2015/0273147 A1 | 10/2015 | Duke et al. |

FOREIGN PATENT DOCUMENTS

| | | |
|---|---|---|
| WO | 2014/106263 A2 | 7/2014 |
| WO | 2015/183689 A1 | 3/2015 |

OTHER PUBLICATIONS

Written Opinion dated Aug. 21, 2017, pertaining to PCT/US2017/029072, filed Apr. 24, 2017, 14 pages.
Jaramillo et al., Prediction of Postprandial Blood Glucose Under Intra-Patient Variability and Uncertainty and Its Use in the Design of Insulin Disposing Strategies for Type I Diabetic Patients, Jul. 22, 2011, pp. 1-178, URL:http://dugi-doc.udg.edu/bitstream/handle.
International Search Report pertaining to PCT application No. PCT/US2017/031661, filed May 9, 2017, 6 pages.
Written Opinion pertaining to PCT application No. PCT/US2017/031661, filed May 9, 2017, 11 pages.
Kovatchev, B.P., et al., Symmetrization of the Blood Glucose Measurement Scale and Its Applications, Diabetes American Diabetes Association, vol. 20., No. 11, Nov. 1, 1997, pp. 1655-1658, USA.
International Search Report pertaining to PCT application No. PCT/US2017/031662, filed May 9, 2017, 6 pages.
Written Opinion pertaining to PCT application No. PCT/US2017/031662, filed May 9, 2017, 9 pages.
Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, No. 5, Sep. 1, 2010, pp. 1146-1155, USA.
International Search Report pertaining to Appln. No. PCT/US2017/019025, filed Feb. 23, 2017, 5 pages.
Written Opinion pertaining to Appln. No. PCT/US2017/019025, filed Feb. 23, 2017, 8 pages.
International Search Report pertaining to Appln. No. PCT/US2017/019013, filed Feb. 23, 2017, 5 pages.
Written Opinion pertaining to Appln. No. PCT/US2017/019013, filed Feb. 23, 2017, 8 pages.
Bruno Sinopoli, et al., Kalman Filtering With Intermittent Observations, DARPA under grant F33615-01-C-1895, 28 pages.
David Di Ruscio, Closed and Open Loop Subspace System Identification of the Kalman Filter, 2009 Norwegian Society of Automatic Control, vol. 30, No. 2, 2009, pp. 71-86, ISSN 1890-1328, Norway.
J. Zico Kolter, et al., A Probabilistic Approach to Mixed Open-loop and Closed-loop Control, with Application to Extreme Autonomous Driving, Computer Science Department, Stanford University, California (kolter@cs.stanford.edu) 7 pages, USA.
Chiara Toffanin, et al., Artificial Pancreas: Model Predictive Control Design from Clinical Experience, Journal of Diabetes Science and Technology, pp. 1470-1483, vol. 7, Issue 6, Nov. 2013, USA.
Signe Schmidt, et al., Model-Based Closed-Loop Glucose Control in Type 1 Diabetes: The DiaCon Experience, Journal of Diabetes Science and Technology, pp. 1255-1264, vol. 7, Issue 5, Sep. 2013, USA.
International Search Report pertaining to Appln. No. PCT/US2017/019030, filed Feb. 23, 2017, 5 pages.
Written Opinion pertaining to Appln. No. PCT/US2017/019030, filed Feb. 23, 2017, 9 pages.
U.S. Non-Final Office Action dated Sep. 5, 2017 pertaining to U.S. Appl. No. 14/677,148, 13 Pages.
U.S. Non-Final Office Action dated May 31, 2018 pertaining to U.S. Appl. No. 15/170,468, 12 pages.

PROBABILITY BASED CONTROLLER GAIN

TECHNICAL FIELD

The present disclosure relates to insulin delivery and more particularly, to a controller for insulin delivery that implements probability based controller gain based on a calculated quality of signal input from a glucose sensor in order to better determine the insulin delivery required to maintain good glucose control of a person.

BACKGROUND

As background, people suffer from either Type I or Type II diabetes in which the sugar level in the blood is not properly regulated by the body. Many of these people may use a continuous glucose monitoring (CGM) to monitor their glucose level on an ongoing basis. In order to perform CGM, a glucose sensor may be placed under the skin which is capable of measuring the glucose level of the person in the interstitial fluid. The glucose sensor may periodically measure the glucose level of the person at a known time interval, such as every one minute, and transmit the results of the glucose measurement result to an infusion pump, blood glucose meter, smart phone or other electronic monitor.

In some cases, the measured glucose results (from the glucose sensor) may contain sensor "noise" which causes them to deviate from the actual glucose level of the person. Sensor noise may be due to, for example, physical movement of the glucose sensor relative to the skin or due to electrical noise which may be inherent in the sensor itself. Furthermore, the glucose sensor may malfunction from time to time, such that the measured glucose results (from the glucose sensor) may be substantially different than the actual glucose level of the person. The glucose sensor may malfunction in this manner due to, for example, failure of the sensor electronics or battery or due to sensor "dropout." Sensor dropout may occur due to physiological problems with the glucose sensor's attachment to the person, such as movement of the sensor relative to the person. Sensor dropout may cause the measured glucose results "drop" to near zero, although the actual glucose level of the person may be much higher.

SUMMARY

In view of the above noted issues and according to the subject matter of the present disclosure, embodiments herein describe a controller for insulin delivery that implements probability based controller gain based on a calculated quality of signal input from a glucose sensor in order to better determine the insulin delivery required to maintain good glucose control of a person.

In accordance with one specific embodiment, disclosed herein is a method for estimating a glucose level of a person having diabetes and selecting automatically open-loop and closed-loop control for a connected therapy delivery device. The method may comprise receiving into a blood glucose management device having a microcontroller a plurality of measured glucose results and corresponding impedance values from a glucose sensor coupled to the person, and using the microcontroller to analyze the plurality of measured glucose results and corresponding impedance values with a probability analysis tool configured to determine a total quality score $Q_{total}$ total that is based on the minimum constraint of a probability of glucose sensor accuracy $P_A$ based on the plurality of measured glucose results and a probability of sensing quality $Q_{ac}$ based on the impedance values. The method may further include using the microcontroller to estimate the glucose level of the person with a recursive filter configured to estimate the glucose level based on the plurality of measured glucose results weighted with the total quality score $Q_{total}$ total and select automatically either open-loop control or closed-loop control for the connected therapy delivery device based on the value of the total quality score $Q_{total}$.

In accordance with another specific embodiment, disclosed herein is an apparatus for estimating a glucose level of a person having diabetes and selecting automatically open-loop and closed-loop control for a connected therapy delivery device, in which the apparatus comprises a microcontroller and a display. The apparatus may comprise the microcontroller being configured to receive a plurality of measured glucose results and corresponding impedance values from a glucose sensor coupled to the person, and analyze the plurality of measured glucose results and corresponding impedance values with a probability analysis tool configured to determine a total quality score $Q_{total}$ total that is based on the minimum constraint of a probability of glucose sensor accuracy $P_A$ based on the plurality of measured glucose results and a probability of sensing quality $Q_{ac}$ based on the impedance values. The microcontroller of the apparatus may be configured to estimate the glucose level of the person with a recursive filter configured to estimate the glucose level based on the plurality of measured glucose results weighted with the total quality score $Q_{total}$ and select automatically either open-loop control or closed-loop control for the therapy delivery device based on the value of the total quality score $Q_{total}$. The microcontroller of the apparatus is electrically coupled to the display such that the microcontroller transmits to the display information related to the estimate of the glucose level of the person and the selected control for the therapy delivery device.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

Figure 1:
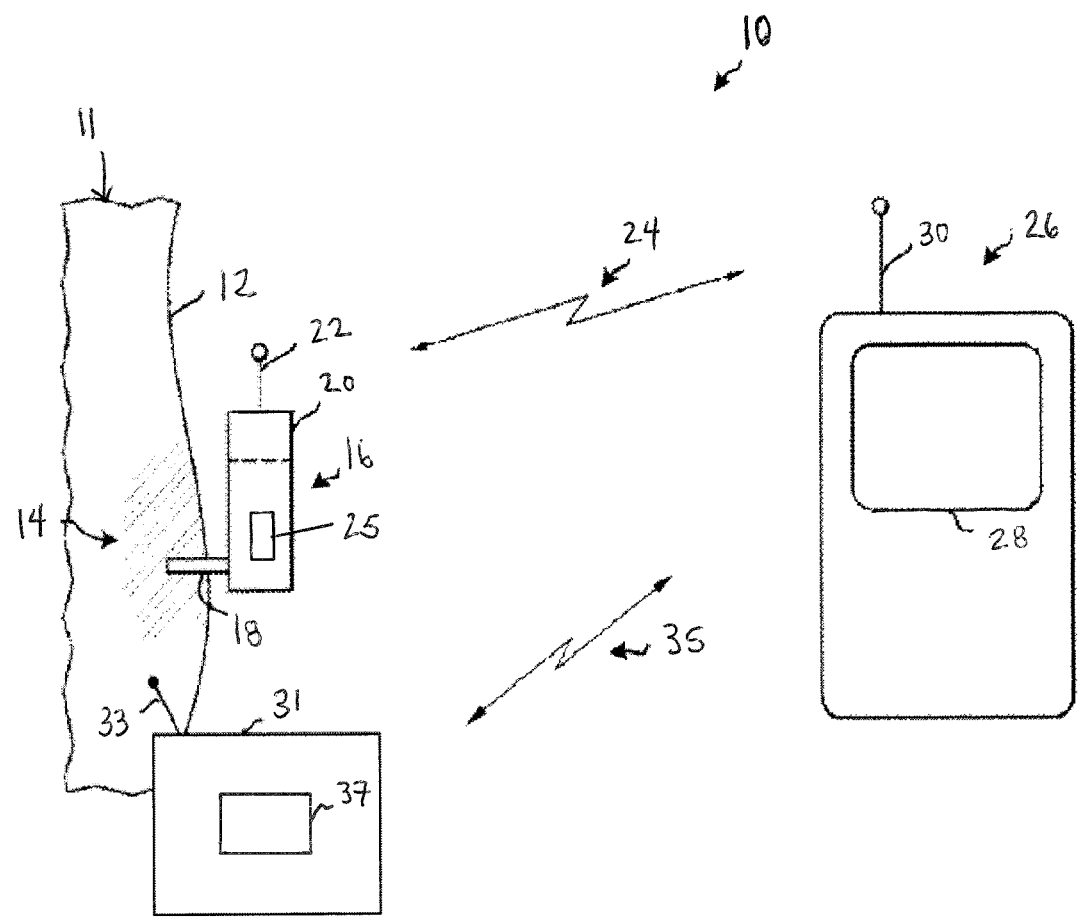
FIG. 1 depicts an exemplary continuous glucose monitoring (CGM) system according to one or more embodiments shown and described herein.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

For the purposes of defining the present disclosure, the "measured glucose results" are the glucose levels of the person as measured by the glucose sensor; the "actual glucose level" is the actual glucose level of the person; and the "estimated glucose level" is the estimated glucose level of the person, which may be based on the measured glucose results.

Referring to FIG. 1, an exemplary continuous glucose monitoring (CGM) system 10 is illustrated for monitoring the glucose level of a person with diabetes (PWD) 11. In particular, CGM system 10 is operative to collect a measured glucose value at a predetermined, adjustable interval, such as every one minute, five minutes, or at other suitable intervals. CGM system 10 illustratively includes a glucose sensor 16 having a needle or probe 18 that is inserted under the skin 12 of the person 11. The end of the needle or probe 18 is positioned in interstitial fluid 14, such as blood or another bodily fluid, such that measurements taken by glucose sensor 16 are based on the level of glucose in interstitial fluid 14. Glucose sensor 16 is positioned adjacent the abdomen of the person or at another suitable location. Furthermore, the glucose sensor 16 may be periodically calibrated in order to improve its accuracy. This periodic calibration may help correct for sensor drift due to sensor degradation and changes in the physiological condition of the sensor insertion site. Glucose sensor 16 may comprise other components as well, including but not limited to a wireless transmitter 20 and an antenna 22. Glucose sensor 16 may alternatively use other suitable devices for taking measurements, such as, for example, a non-invasive device (e.g., infrared light sensor). Upon taking a measurement, glucose sensor 16 transmits the measured glucose value via a communication link 24 to a computing device 26, illustratively a blood glucose (bG) management device 26. The bG management device 26 may also be configured to store in memory 39 a plurality of measured glucose results received from the glucose sensor 16 over a period of time as well as corresponding impedance measurements from an impedance measuring sensor 25.

CGM system 10 further includes a therapy delivery device 31, illustratively an insulin infusion pump 31, for delivering therapy (e.g., insulin) to the person. Infusion pump 31 is in communication with management device 26 via a communication link 35, and management device 26 is able to communicate bolus and basal rate information to infusion pump 31. Infusion pump 31 includes a catheter 33 having a needle that is inserted through the skin 12 of the PWD 11 for injecting the insulin. Infusion pump 31 is illustratively positioned adjacent the abdomen of the person or at another suitable location. Similar to glucose sensor 16, infusion pump 31 also includes a wireless transmitter and an antenna for communication with management device 26. Infusion pump 31 is operative to deliver basal insulin (e.g., small doses of insulin continuously or repeatedly released at a basal rate) and bolus insulin (e.g., a surge dose of insulin, such as around a meal event, for example). The bolus insulin may be delivered in response to a user input triggered by the user, or in response to a command from management device 26. Similarly, the basal rate of the basal insulin is set based on user input or in response to a command from management device 26. Infusion pump 31 may include a display 37 for displaying pump data and a user interface providing user controls. In an alternative embodiment, infusion pump 31 and glucose sensor 16 may be provided as a single device worn by the patient, and at least a portion of the logic provided by processor or microcontroller may reside on this single device. Bolus insulin may also be injected by other means, such as manually by the user via a needle.

Communication links 24, 35 are illustratively as being wireless, such as a radio frequency ("RF") or other suitable wireless frequency, in which data and controls are transmitted via electromagnetic waves between sensor 16, therapy delivery device 31, and management device 26. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. Furthermore, each communication link 24, 35 may facilitate communication between multiple devices, such as between glucose sensor 16, computing device 26, infusion pump 31, and other suitable devices or systems. Wired links may alternatively be provided between devices of system 10, such as, for example, a wired Ethernet link. Other suitable public or proprietary wired or wireless links may be used.

Figure 2:
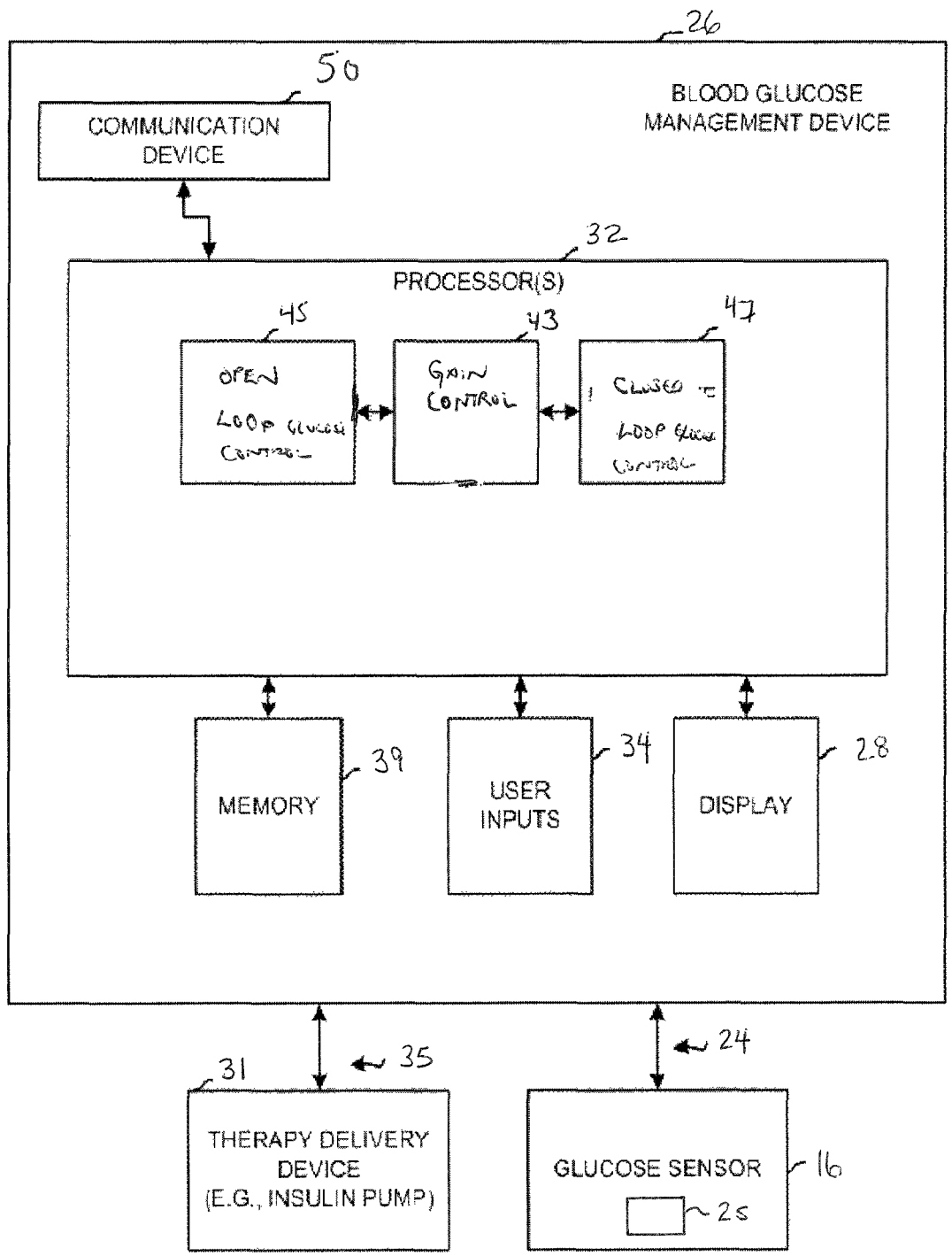
FIG. 2 depicts a blood glucose (bG) management device according to one or more embodiments shown and described herein.

FIG. 2 illustrates an exemplary bG management device 26 of the CGM system 10 of FIG. 2. Management device 26 includes at least one microprocessor or microcontroller 32 that executes software and/or firmware code stored in memory 39 of management device 26. The software/firmware code contains instructions that, when executed by the microcontroller 32 of management device 26, causes management device 26 to perform the functions described herein. Management device 26 may alternatively include one or more application-specific integrated circuits (ASICs), field-programmable gate arrays (FPGAs), digital signal processors (DSPs), hardwired logic, or combinations thereof. While management device 26 is illustratively a glucose monitor 26, other suitable management devices 26 may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although management device 26 is illustrated as a single management device 26, multiple computing devices may be used together to perform the functions of management device 26 described herein.

Memory 39 is any suitable computer readable medium that is accessible by microcontroller 32. Memory 39 may be a single storage device or multiple storage devices, may be located internally or externally to management device 26, and may include both volatile and non-volatile media. Further, memory 39 may include one or both of removable and non-removable media. Exemplary memory 39 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by management device 26.

Management device 26 further includes a communication device 50 operatively coupled to microcontroller 32. Communication device 50 includes any suitable wireless and/or wired communication module operative to transmit and receive data and controls over communication links 24, 35 between device 26 and glucose sensor 16 and infusion pump 31. In one embodiment, communication device 50 includes an antenna 30 (FIG. 1) for receiving and/or transmitting data wirelessly over communication links 24, 35. Management device 26 stores in memory 39 measured glucose results and other data received from glucose sensor 16 and/or infusion pump 31 via communication device 50.

Management device 26 includes one or more user input device(s) 34 for receiving user input. Input device(s) 34 may include pushbuttons, switches, a mouse pointer, keyboard, touchscreen, or any other suitable input device. Display 28 is operatively coupled to microcontroller 32, and may comprise any suitable display or monitor technology (e.g., liquid crystal display, etc.) configured to display information provided by microcontroller 32 to a user. Microcontroller 32 is configured to transmit to display 28 information related to the detected glucose state of the person, the risk associated with the glucose state, and basal rate and bolus information. The glucose state may include the estimated glucose level and the estimated rate-of-change of the glucose level, as well as an estimate of the quality or uncertainty of the estimated glucose level. Moreover, the displayed information may include warnings, alerts, etc., regarding whether the estimated or predicted glucose level of the person is hypoglycemic or hyperglycemic. For example, a warning may be issued if the person's glucose level falls below (or is predicted to fall below) a predetermined hypoglycemic threshold, such as 50 to 70 milligrams of glucose per deciliter of blood (mg/dl). Management device 26 may also be configured to tactilely communicate information or warnings to the person, such as for example by vibrating.

In one embodiment, management device 26 is in communication with a remote computing device (not shown), such as at a caregiver's facility or a location accessible by a caregiver, and data (e.g., glucose data or other physiological information) is transferred between them. In this embodiment, management device 26 and the remote device are configured to transfer physiological information through a data connection such as, for example, via the Internet, cellular communications, or the physical transfer of a memory device such as a diskette, USB key, compact disc, or other portable memory device.

Microcontroller 32 includes gain control module 43 that is the program logic that maintains the glucose state of a person at a target glucose state based on insulin delivery controlled via either open-loop glucose control 45 or closed-loop glucose control 47. It is to be appreciated that the therapy delivery device 31, via communication link 35, operates with either open-loop glucose control 45 or closed-loop glucose control 47 as is selected and periodically updated by the gain control module 43 via a total quality score, $Q_{total}$, calculated upon receiving signal inputs from the glucose sensor 16 and/or the impedance sensor 25. The target glucose state is illustratively an optimal or ideal glucose state having no associated hazard or risk, such as a glucose level of 112.5 mg/dl and a glucose rate-of-change of zero, although any suitable target glucose state may be identified. In the illustrated example provided hereafter in later sections, the total quality score is based on an analysis the gain control module 43 causes the microcontroller 32 to run on the signal input characteristic(s) and data received from the glucose sensor 16, i.e., on a plurality of measured glucose results, and associated impendence values from the impedance sensor 25, and uses the resulting information from the analysis to select either open-loop glucose control 45 or closed-loop glucose control 47 as well as provide such information on a display 28 to indicated in which mode (open- or closed-loop) the therapy delivery device 31 is operating currently to the PWD 11. A discussion of the information provided by the signal inputs from the glucose sensor 16 and/or an impedance sensor 25.

Figure 3A:
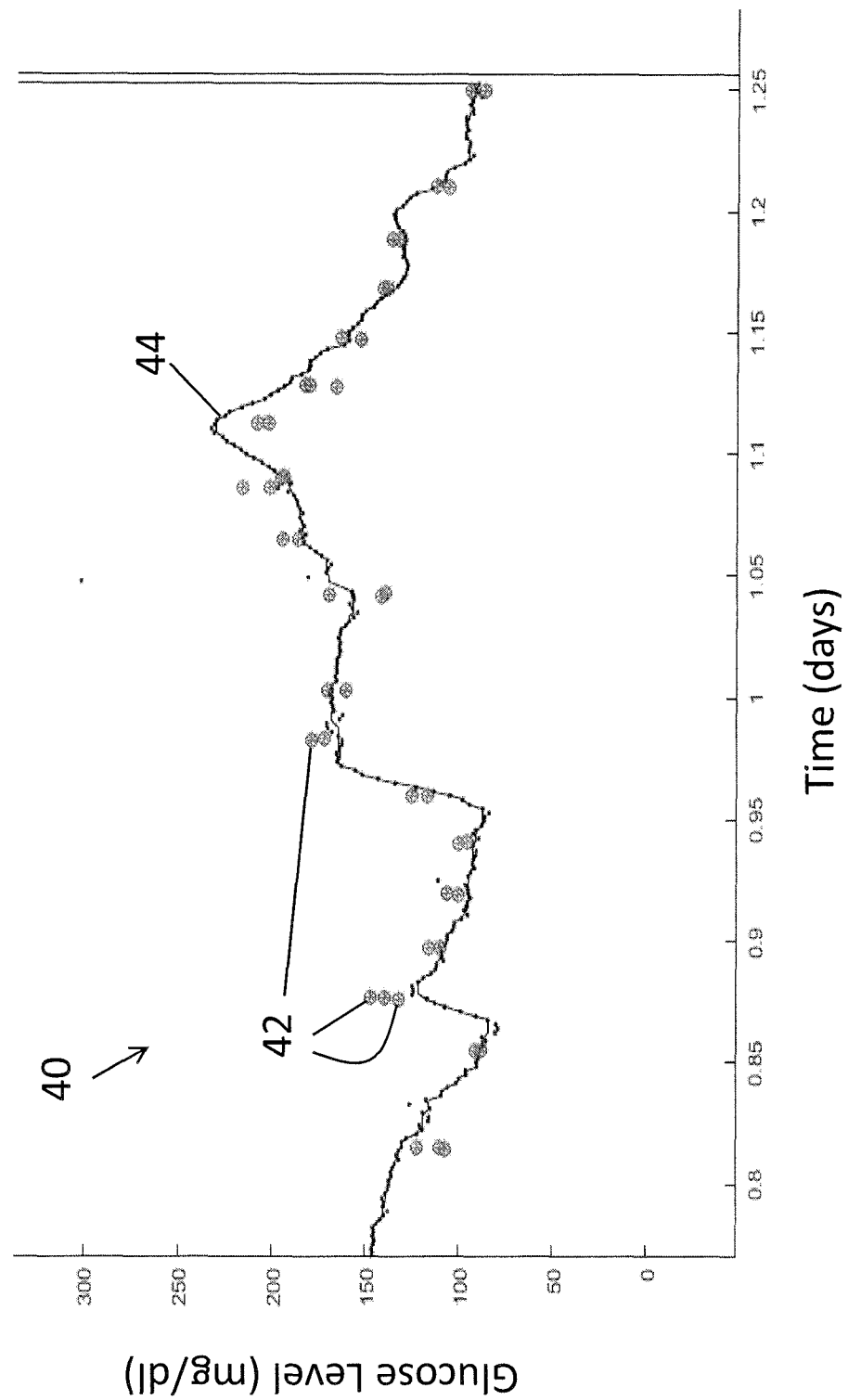
FIG. 3A depicts a graph of measured glucose results and actual glucose levels of a person according to one or more embodiments shown and described herein.
Figure 3B:
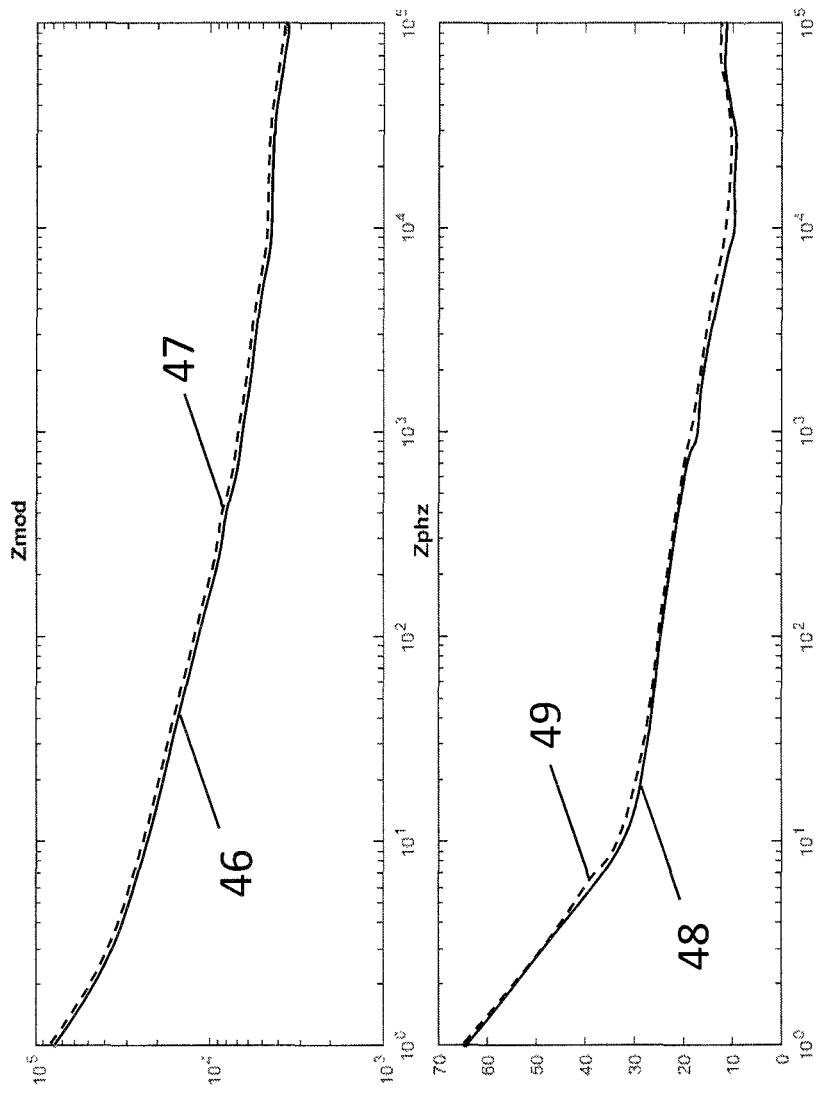
FIGS. 3B and 3C each depict a graph of impedance measurements made with a subcutaneous glucose sensor according to one or more embodiments shown and described herein.

FIG. 3A depicts an example of a graph of measured glucose results 40 from a glucose sensor 16 coupled to a person with diabetes. The shown large circles 42 show glucose values measured with a standard blood glucose measurement system, such as may be used for the calibration of the continuous glucose sensor. The connected line of small circles 44 show the glucose values measured by the subcutaneous glucose sensor, such as sensor 16 (FIG. 1). Until a time shortly after the time indicated by 1.25 (days following placement of the sensor) the sensor 16 tracks the reference values well, demonstrating good performance. During this time, impedance measurements made with the sensor 16 show a pattern seen in FIG. 3B. Solid lines 46 and 48 show the magnitude "Zmod" (in Ohms) and the phase angle "Zphz" (in degrees) of impedance, respectively, measured by the sensor, plotted vs. frequency (Hz). The overlaying dashed lines 47 and 49 for the magnitude and the phase angle, respectively, show the result of fitting the impedance data to an equivalent circuit model which describes the sensor 16. The model fits the measured data well from 1 Hz to 10 kHz. This fitting result is an indication that the sensor 16 is functioning well, in agreement with the comparison with the reference values in FIG. 3A. The degree of agreement between the measured data and the model is quantified by the lack-of-fit parameter ("error") in the model statistics, in which good agreement is associated with a small value of lack-of-fit, or error as show below in an illustrated example of Table 1.

TABLE 1

| EIS Model | |
| --- | --- |
| | rwcx |
| f_Max(Hz) | 1e+04 |
| f_Min(Hz) | 1 |
| error | 0.002849 |
| Rs | 2625 |
| W1R | 1.905e+04 |
| W1T | 0.02389 |
| W1P | 0.31 |
| CPE2-T | 2.905e−06 |
| CPE2-P | 0.88 |

Figure 3C:
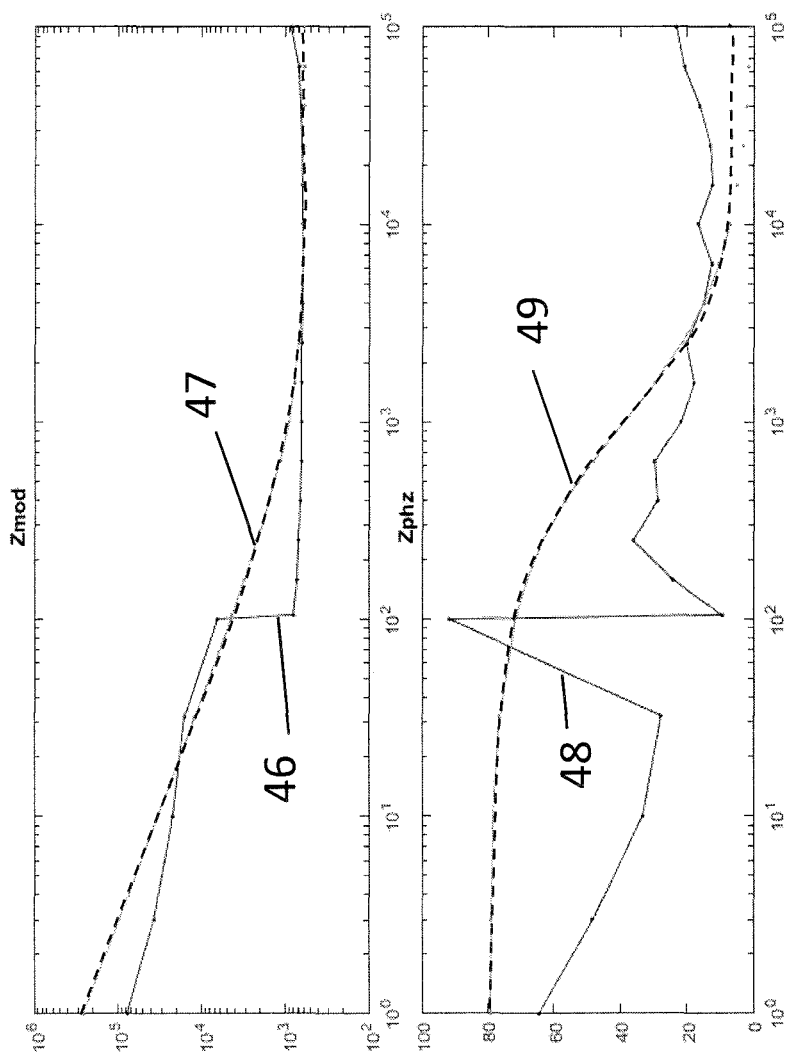

In the illustrative embodiment of FIG. 3A, shortly after time 1.25 days, the sensor 16 malfunctions and shows values which are not reasonable. FIG. 3C shows the impedance measurements made with the sensor at this time, again depicted by lines 46, 48 for the measured magnitude and the measured Phase angle, respectively. The measured values depicted by lines 46, 48 and the fit to the equivalent circuit model depicted by lines 47, 49 for the model magnitude and the model phase angle, respectively, deviate significantly. This deviation is an indicator of unreliable sensor performance, and is quantified by the lack-of-fit parameter ("error") in the model statistics as show below in the illustrated example of Table 2.

TABLE 2

| EIS Model | |
|---|---|
| | rwcx |
| f_Max(Hz) | 1e+04 |
| f_Min(Hz) | 1 |
| error | 5.89 |
| Rs | 602.5 |
| W1R | 25 |
| W1T | 10 |
| W1P | 0.31 |
| CPE2-T | 7.811e−07 |
| CPE2-P | 0.8799 |

In view of the above, a sensor in which the impedance and/or phase angle measurements no longer agree with the form of the known equivalent circuit model of the sensor can be determined to be malfunctioning and indicated as not delivering reliable data. Such graphical depictions of the information illustrated by FIGS. 3A-3C in some embodiments may be provided by the microcontroller 32 to a display, e.g., to one or both of displays 28 and 37, for reviewing by a user if desired.

It is to be appreciated that the greatest barrier to adoption of an automatic control strategy for insulin delivery systems has been the uncertainty in the input data, i.e. the glucose values, from a continuous glucose sensor(s). Great effort has been made in improving the accuracy and reliability. For example, even with impedance data being used to adjust the data from the glucose sensor to improve the accuracy of the reported value, a reliability of 100% is probably not likely to be achieved. For this reason, the gain control module 43 evaluates the quality of the sensor data, and accounts for the quality in the control algorithm. Specifically, the inventors have discovered that a probability score derived from the time course of sensor data and used to adapt the gain of a statistical filter can improve the quality of the reported value.

For the above reason and according to various embodiments disclosed herein, the embodiments described herein generally relate to methods and systems for insulin delivery and more particularly, to a controller for insulin delivery that implements probability based controller gain based on a calculated quality of signal input from a glucose sensor in order to better determine the insulin delivery required to maintain good glucose control of a person. Specifically, systems and methods are described that assess the quality of data being evaluated in terms of a total quality score $Q_{total}$ total from a set of quality metrics, e.g., of signal input characteristic(s) and data received from the glucose sensor 16 and/or an impedance sensor 25. The total quality score $Q_{total}$ total has a value that ranges from zero (0) to (one) 1, and is used to alter gain of the microcontroller 32 to provide an increased level of safety when the quality score is low, and to improve microcontroller performance and glycemic control when the quality score is high.

For example, in one illustrated implementation, in the case of a sensor 16 with a total quality score, $Q_{total}=0$ (or $0 \leq Q_{total} \geq T$), the microcontroller 32 if operating in closed-loop glucose control 47, in which insulin delivery adjustments are made automatically by the microcontroller 32 based on the received input from the sensors 16 and 25, would fall back to a safer, open-loop mode of operation, i.e., open-loop glucose control 45 (FIG. 2), in which adjustments are made by the user and as recommended to the user by pre-programmed time profiles. In the case of the total quality score $Q_{total}$ being greater than a threshold value T and/or equal to one (1), i.e., $T < Q_{total} \leq 1$, the microcontroller 32 acts more aggressively to manage glycemia with the certainty that the sensor data will enable the system to deliver the proper amount of insulin, thereby allowing, e.g., the system 10 to function in optimal closed-loop glucose control 47 with optimal safety. In some embodiment, the threshold value T is preset in memory to a value that indicates a high probability (e.g., T=0.9) that the sensor data is accurate enough to enable the system to deliver the proper amount of insulin, and in other embodiments may be set and/or adjusted by the PWD 11 or a health care provider to a particular value that sufficiently provides a threshold between open-loop and closed-loop control for the PWD 11. In a specific embodiment, the user is notified, e.g., on display 37 by the microcontroller 32 when the microcontroller switches the therapy delivery device 31 back automatically to closed-loop control from open-loop control when $Q_{total}$ is close to or at 1.

Figure 4:
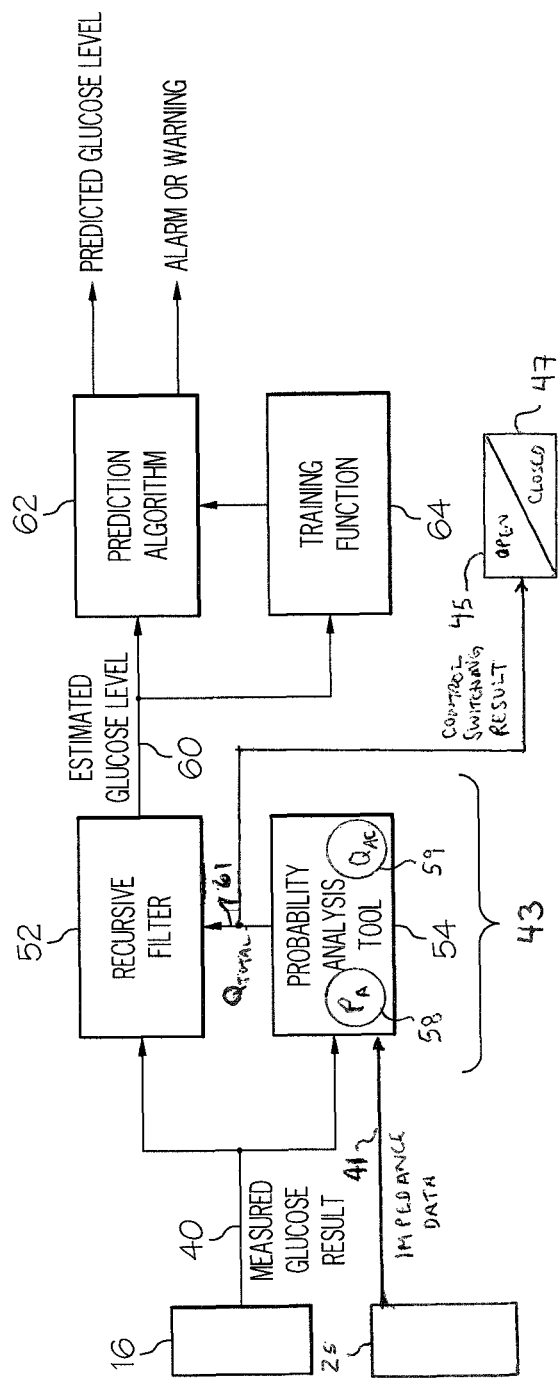
FIG. 4 depicts gain control logic providing a probability analysis tool and a recursive filter according to one or more embodiments shown and described herein.

FIG. 4 depicts various modules of and inputs to the gain control module 43 that are used to determine the best insulin delivery control, i.e., open-loop or closed-loop control, that will maintain good glucose control of the PWD 11. The gain control module 43 receives the measured glucose results 40 from the glucose sensor 16 that is coupled to the PWD 11 as well as data from an impedance sensor 25. The glucose sensor 16 and impedance sensor 25 may be configured to periodically measure the glucose level and impedance of the person and transmit the measured glucose results 40 and associated impedance measurements 41 to the gain control module 43 (e.g., via a communication link 24). The period of sensing and transmitting by the glucose sensor 16 and impedance sensor 25 may be a period selected from 1 to 10 minutes (e.g., 1, 5 or 10 minutes), and may be factory set and/or adjustably set by the PWD 11 or a health care provider, e.g., via the user inputs 34 of the blood glucose management device 26.

As depicted by FIG. 4, the gain control module 43 may comprise a probability analysis tool 54 and a recursive filter 52. The probability analysis tool 54 may be configured to receive the measured glucose results 40 as well as the associated impedance data 41, e.g., AC impedance, sensed by the impedance sensor 25 and associated with each measured glucose result 40. The probability analysis tool 54 then determines a total quality score $Q_{total}$ 61 from a set of computed quality metrics based on such received measured glucose results 40 and associated impedance data 41. For example, one such quality metric may be a probability of glucose sensor accuracy $P_A$ 58 computed from the received measured glucose results 40. The probability of glucose sensor accuracy $P_A$ 58 is a calculated probability value that the glucose sensor 16 is functioning normally (i.e., not malfunctioning). Commonly owned U.S. Pat. No. 8,843,321 discusses how the probability of glucose sensor accuracy $P_A$ 58 may be computed from received measured glucose results (the disclosure of which is herein fully incorporated by reference). Another one of the quality metrics that is used in determining the total quality score $Q_{total}$ total is a sensor quality score $Q_{AC}$ 59 derived from AC impedance measurements, i.e., the probability that the glucose sensor 16 is properly contacting the PWD 11 and providing non-erroneous sensor values. The total quality score $Q_{total}$ 61 may also use other metrics related to the quality of a sensor measurement. Accordingly, the output of the probability analysis tool 54, i.e., the total quality score $Q_{total}$ 61 may be used to distinguish between sensor noise and poor sensing characteristics, which each may have a normal distribution, and sensor malfunction which may not be normally distributed, as well as for selecting in which control mode to operate the therapy delivery device 31, either open-loop glucose control 45 or closed-loop glucose control 47 as discussed previously above. A discussion on how the probability analysis tool 54 outputs the total quality score $Q_{total}$ 61 follows hereafter.

The probability analysis tool 54 may comprise any number of mathematical algorithms which are capable of analyzing the measured glucose results 40, the AC impedance measurements 41, and/or changes thereof and calculating a minimum total quality score $Q_{total}$ 61 from the above noted set of quality metrics. For example, a Hidden Markov Model is used to estimate the minimum total quality score $Q_{total}$ 61 based on the measured glucose results 40 and the AC impedance measurements 41. As discussed above, the output of the probability analysis tool 54 has a value for $Q_{total}$ ranging from 0 to 1 that is related to the probability that the sensor is functioning normally and providing data sufficiently safe for the microcontroller 32 to run in closed-loop glucose control 47 and deliver a proper amount of insulin to the PWD 11 to maintain the glucose state of a person at the target glucose state. The probability analysis tool 54 may be also configured to receive other types of data on which the total quality score $Q_{total}$ 61 may be based, such as when the person eats a meal, when the person exercises, and when insulin is delivered to the person. A discussion on how the sensor quality score $Q_{AC}$ 59 is derived now follows hereafter.

The sensor quality score $Q_{AC}$ 59 may be derived from the AC impedance measurements (AC) that were provided by the impedance measuring device 25 by evaluating the lack-of-fit of the measured values with the known equivalent circuit model. For example, the "error" (E) may be used in the following equation:

$$Q_{AC} = 0.5*(1-\tan h(a*\log (b*E)),$$

to compute a value between 1 (for a very low E) and zero (for a high E). The parameters a and b may be selected to choose the location of the 0.5 value (1/b) and the rate of change at the 0.5 value (a). Alternatively, the value of $Q_{AC}$ may be derived from the parameters resulting from fitting the data to the equivalent circuit model. The parameters provide a quantitative comparison of the electrochemical properties of the sensor as compared to its previous or factory-derived batch values. The deviation from the predetermined values can be summed into an error term, and from the error term a $Q_{AC}$ computed as in the previous case. The sensor quality score $Q_{AC}$ 59 derived from the AC impedance measurements is then combined with the $P_A$ 58 value to and the total quality score $Q_{total}$ 61 is calculated by finding the minimum quality score from the set of quality metrics, according to the following equation:

$$Q_{total} = \min(P_A, Q_{AC}, \ldots).$$

It is to be appreciated that the output of the probability analysis tool 54, i.e., the total quality score $Q_{total}$ 61 can be take on a number of different forms such as a state machine, Bayesian models, or other algorithms. In one embodiment, the probability analysis tool 54 may take the form of a simple state machine, in which the total quality score $Q_{total}$ 61, as well as the probability of glucose sensor accuracy $P_A$, may always be in the set {0,1} (i.e., $Q_{total}$ 61 and $P_A$ 58 are each either 0% or 100%, depending on the state of the state machine). In this example and as disclosed in the above referenced patent, for the probability of glucose sensor accuracy $P_A$, the system 10 would transfer to a state of sensor inaccuracy, $T_{A \to I}$, if the $\Delta$CG (i.e., the change in the current measured glucose result from the previous measured glucose result) is less than a certain negative threshold, $\tau_1$, and transfer back to a state of sensor accuracy, $T_{I \to A}$, if the $\Delta$CG is greater than a certain positive threshold, $\tau_2$, or if the sensor CG value (i.e., the current measured glucose result) are within physiologically possible glucose values ($g_0$ and $g_{max}$) and a certain amount of time has elapsed since the transition to the state of sensor inaccuracy, $\Delta t_{A \to I} > \tau_3$. This may be represented mathematically as:

$T_{A \to I}$ if $\Delta CG < \tau_1$ $T_{I \to A}$ if $\Delta CG > \tau_2$ or ($g_0 < CG < g_{max}$ and $\Delta t_{A \to I} > \tau_3$)

If neither of these transfer conditions is met, then the state machine may remain in its current state. This is just one example of the probability analysis tool 54 taking the form of a state machine. The probability analysis tool 54 may take on other forms as well.

In another embodiment, the probability analysis tool 54 may comprise a hidden Markov model having two states for the glucose sensor: 1) the state wherein the glucose sensor is accurate denoted by "$S_A$"; and 2) the state wherein sensor is inaccurate denoted by "$S_I$". The hidden Markov model may provide state transition functions that define the probability of transitioning from state $S_A$ to state $S_I$, such as the following function:

$$P_{A \to I} = \min\left[\left(1 - \frac{1}{1 + e^{-(\Delta CG + a_1)/a_2}}\right) + \left(1 - \frac{1}{1 + e^{-(CG + a_3)/a_4}}\right), 1\right],$$

where "CG" is the current measured glucose result, "$\Delta$CG" is the change from the previous measured glucose result to the current measured glucose result, and $\alpha_1$ to $\alpha_4$ are constants which depend on the characteristics of the glucose sensor. The range of output values for this function are zero to one, where zero represents 0% probability and one represents 100% probability of sensor accuracy. The "min" function takes the minimum value of the mathematical expression and the number one (i.e., 100%). This transition function may be based on the current CG and $\Delta$CG values. Furthermore, the transition function may be a sigmoid, wherein the parameters $\alpha_1$ and $\alpha_3$ control the location of the sigmoid transition, and parameters $\alpha_2$ and $\alpha_4$ control the slope of the sigmoid. These parameters may be tuned for a specific person and/or sensor batch.

Continuing with the example of the hidden Markov model, the probability of remaining in state $S_I$ (when the current state is $S_I$) may be $$P_{I \to I} = \max\left[\gamma P_{I_{k-1}} - \left(\frac{1}{1 + e^{-(\Delta CG + a_5)/a_6}}\right), 0\right]$$

and is only a function of the $\Delta$CG value and the previous probability $P_{I_{k-1}}$ of being in or transitioning to state $S_I$. The range of output values for this function are zero to one, where zero represents 0% probability and one represents 100% probability. The "max" function takes the maximum value of the mathematical expression and the number zero (i.e., 0%). The parameter "γ" is a decay term that is less than one and designed to gradually transition the state of the hidden Markov model back to $S_A$ if there is no evidence from the CG and ΔCG values to remain in $S_I$. The parameter γ may be a constant and may be related to the probability of remaining in $S_I$ when ΔCG is relatively normal. For example, γ may be selected so that the hidden Markov model remains in $S_I$ for approximately 10 minutes when ΔCG is relatively normal. This probability function also includes a sigmoid function that detects rapid rises in the CG signal that are associated with a return to $S_A$. The parameter $\alpha_5$ controls the location of the sigmoid transition, and parameter $\alpha_6$ controls the slope of the sigmoid. Both of these parameters may be tuned for a specific person and/or sensor batch.

The current probability $P_I$ of transitioning to $S_I$ is either $P_{A \to I}$ or $P_{I \to I}$, depending on whether the current state is $S_A$ or $S_I$. The current probability $P_I$ of the glucose sensor being inaccurate (i.e., being is $S_I$) may be $(S_A \times P_{A \to I}) + (S_I \times P_{I \to I})$. Note that the state ($S_A$ or $S_I$) is "1" when in that state and "0" otherwise. This includes the probability of transitioning to $S_I$ ($P_{A \to I}$) given the probability of being in $S_A$, and the probability of remaining in $S_I$ times the probability of currently being in $S_I$. The value of $P_{I \to I}$ is equal to $1 - P_{I \to A}$, and the probability of the sensor being accurate is simply $P_A = 1 - P_I$. Thus, for this example, the probability of glucose sensor accuracy may be $$P_A = 1 - [(S_A \times P_{A \to I}) + (S_I \times P_{I \to I})].$$

Figure 5:
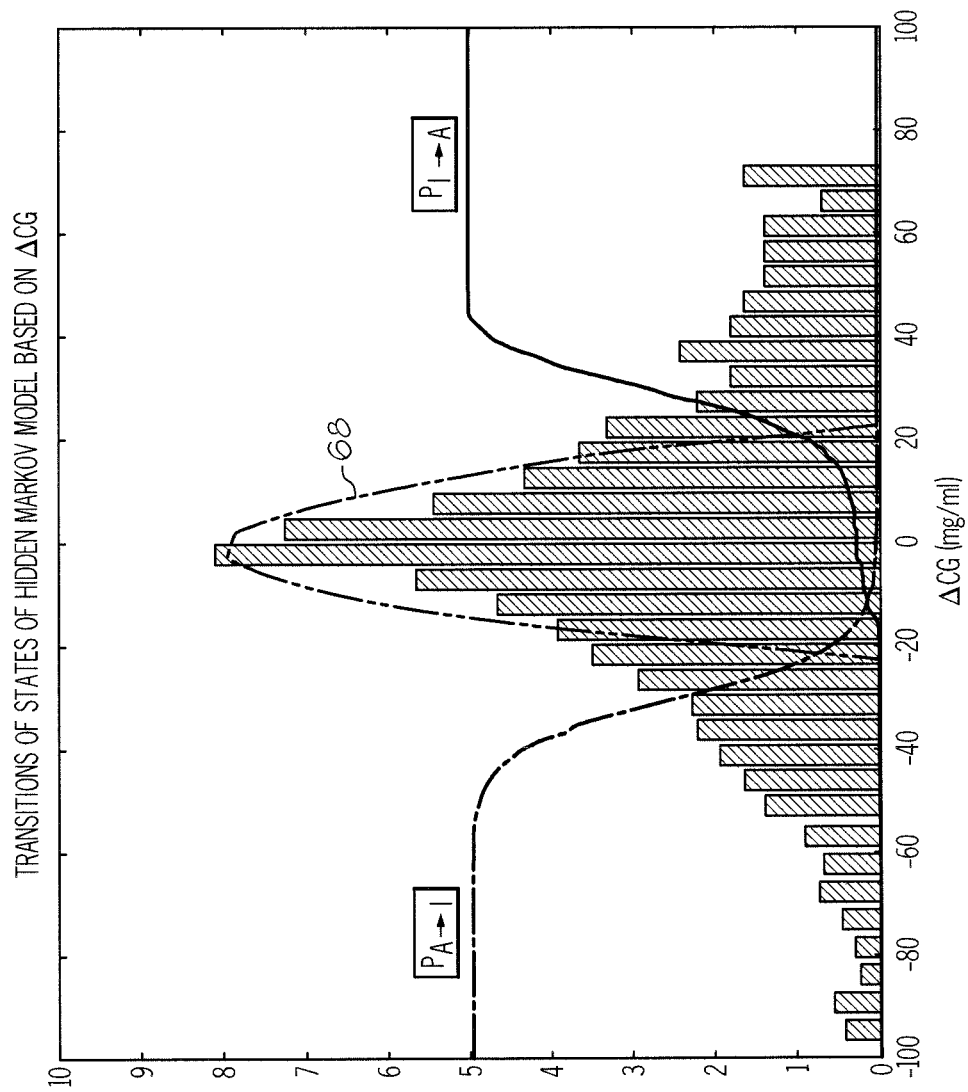
FIG. 5 depicts state transitions for the hidden Markov model according to one or more embodiments shown and described herein.

FIG. 5 depicts a graphical representation of the two transition functions, $P_{A \to I}$ and $P_{I \to A}$ (i.e., $1 - P_{I \to I}$, the probability of transitioning from $S_I$ to $S_A$ when the current state is $S_I$), over a histogram of ΔCG. The histogram includes a Gaussian-shaped component 68 centered about zero with two tails associated with the transitions in and out of sensor malfunction. The two transition functions are plotted over the histogram to show that they may be tuned to trigger on the tails of the histogram. The Gaussian-shaped component 68 may represent the range of ΔCG values which may occur during normal operation of the glucose sensor. The ΔCG values located inside the Gaussian-shaped component 68 may be due to sensor noise, for example. The ΔCG values located outside and to the left of the Gaussian-shaped component 68 may be due to sensor transitioning from $S_A$ to $S_I$. The shape of this distribution may be used to characterize a batch of glucose sensors after production and used to code the sensors. That is, the transition functions ($P_{A \to I}$ and $P_{I \to I}$) may be adjusted (by adjusting $\alpha_1$ to $\alpha_6$ parameters) to correspond to the Gaussian-shaped component 68 for a particular batch of glucose sensors. Thus, the hidden Markov model may be used to determine the probability of sensor being accurate, $P_A$, based solely on the measured glucose results and changes thereof.

Figure 6:
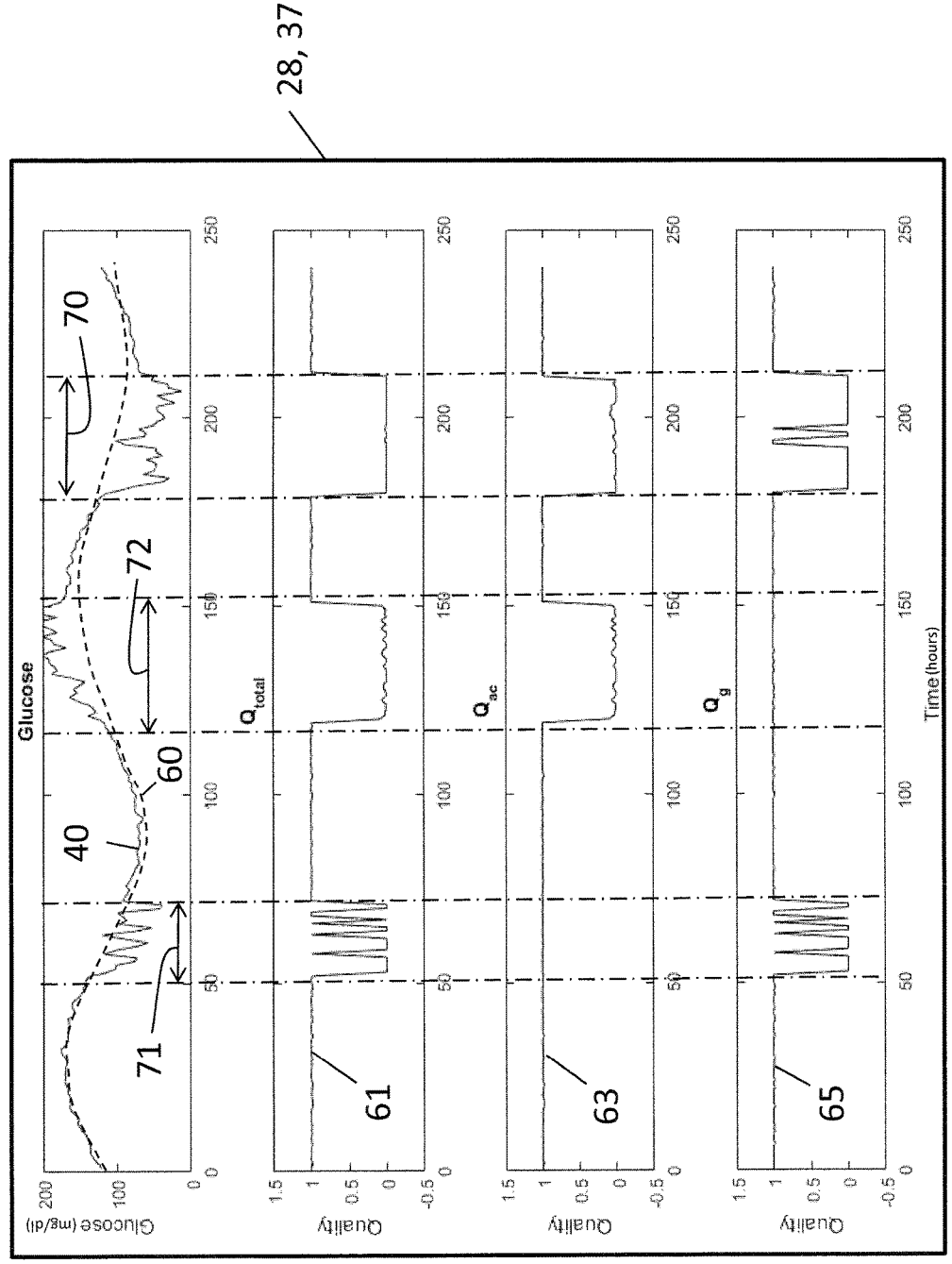
FIG. 6 graphically illustrates operation of the hidden Markov model during presence of a glucose sensor malfunction, glucose sensor noise and reduced sensing quality according to one or more embodiments shown and described herein.

FIG. 6 illustrates a number of graphs which show an example of the operation of the hidden Markov model during the presence of a glucose sensor malfunction in time period 70, glucose sensor noise in time period 71, and reduced sensing quality in time period 72, e.g., due to poor contact of the glucose sensor 16 with the PWD 11. Such graphical depictions of the information illustrated by FIG. 6 in some embodiments may be provided individually or together (as depicted), by the microcontroller 32 to a display, e.g., to one or both of displays 28 and 37, for reviewing by a user if desired.

In FIG. 6, the uppermost "Glucose" graph includes the measured glucose results (solid line) 40 overlaid with an estimated glucose level (dashed line) 60 of the person from whom the trace of glucose results 40 were measured by the sensor 16. Additionally in FIG. 6, the resulting total quality score $Q_{total}$ 61 is plotted below and aligned in time with a "Glucose" trace of the glucose results 40. During the depicted time period 70 the glucose sensor 16 may have a malfunction, i.e., $P_A$ 58 as determined by the hidden Markov model may decrease from approximately 100% (as indicated by a "1" on the "Quality" y-axis immediately before and after time period 70) to near 0% (or a value of zero as indicated on the Quality axis) during time period 70, thus causing the measured glucose results 40 to become inaccurate at the same time. This indication is due to a detection in the hidden Markov model of the rapid decline in the value of the measured glucose results 40 at the beginning of time period 70 (i.e., when the malfunction first occurs) that results from an assessment made by the microcontroller 32 via the gain control module 43 of low or zero sensor impedance and glucose measurement qualities. The assessment results are indicated by the "$Q_{ac}$" and "$Q_g$" plots 63 and 65, respectively, depicted in FIG. 6 and in which plot 63 depicts the values of $P_A$ 58 that are based on the measured glucose results 40, and plot 65 is the values of $Q_{AC}$ 59 that are based on the corresponding AC impedance and/or phase angle measurements 41.

Still referring to FIG. 6, at the end of time period 70, the glucose sensor 16 may begin to operate normally (i.e., the measured glucose results 40 become accurate again) and the total quality score $Q_{total}$ 61 may increase back to approximately 100% again. As before, this may be due to detecting in the hidden Markov model of a rapid increase in the value of the measured glucose results 40 at the end of time period 70 (i.e., when the glucose sensor 16 returns to normal operation) via an assessment by the microcontroller 32 via the gain control module 43 of the sensor impedance and glucose measurement qualities being near or at 100% (or 1). This rapid increase is indicated by the sensor accuracy quality "$Q_{ac}$" plot 63 and the sensor measurement quality "$Q_g$" plot 65 depicted in FIG. 6 after time period 70. The rate of change of the total quality score $Q_{total}$ 61, may depend on how quickly the glucose sensor transitions from malfunctioning (inaccurate) to normal (accurate) operation, i.e., rate $P_A$ 58 is changing from near 0% (or 0) to approximately 100% (or 1) and $Q_{AC}$ remains also approximately 100% (or 1). For example, if the transition is relatively fast, $P_A$ 58 may transition quickly from near 100% to approximately 0%. However, if the glucose sensor transitions slowly from malfunctioning to normal operation, $P_A$ 58 may also transition slowly from near 0% to approximately 100%. The decay term γ (found in the $P_{I \to I}$ equation) may permit $P_A$ 58 to gradually transition back to $S_A$ if there is little or no evidence from the CG and ΔCG values to remain in $S_I$.

Referring still to FIG. 6, glucose sensor noise, which is shown as occurring during time period 71, may also cause the total quality score $Q_{total}$ 61 to decrease, depending on the severity and level of the noise. As depicted in FIG. 6, the glucose sensor noise during time period 71 may cause the total quality score $Q_{total}$ 61 to decrease sporadically between good (100% or 1) and bad (0% or 0) sensing quality. Likewise, in time period 72, poor sensing quality due to improper sensor placement/contact (as indicated by the $Q_{ac}$ plot 63 in this time period being generally at 0% or 0), may also cause the total quality score $Q_{total}$ 61 to decrease, depending on the severity and level of the noise. As depicted in FIG. 6, the glucose sensor noise during time period 71 may cause the total quality score $Q_{total}$ 61 to decrease sporadically between good (100% or 1) and bad (0% or 0) sensing quality. Of course, both glucose sensor malfunction and sensor noise as well as poor sensing quality may have varying levels of amplitude and/or duration as evident in corresponding time periods 70, 71 and 72 of the glucose results 40. Furthermore, glucose sensor malfunction, sensor noise and poor sensing quality may temporally overlap, either in part or completely. The hidden Markov model may be configured such that the microcontroller 32 determines the total quality score $Q_{total}$ 61 under any of these conditions, such as by finding the minimum between $P_A$ 58 and $Q_{ac}$ 59. As will be discussed hereinafter, the minimum total quality score $Q_{total}$ 61 may be used in a recursive filter by the microcontroller 32 in order to minimize the effect of glucose sensor malfunction, glucose sensor noise or poor sensing quality so as to provide an accurate estimate the actual glucose level of the person even in the presence of glucose sensor malfunction, sensor noise and/or poor sensing quality.

Referring again to FIG. 4, the gain control module 43 may comprise a recursive filter 52 which may be used to estimate the glucose level of the person. As depicted, the input to the recursive filter 52 is the output from the probability analysis tool 54, i.e., the minimum total quality score $Q_{total}$ 61 resulting from the set of quality metrics i.e., resulting from $P_A$ 58 based on the measured glucose results 40, and $Q_{AC}$ 59 based on the corresponding AC impedance measurements 41. Examples of recursive filters which may be used include a Kalman filter and an Extended Kalman filter (EKF). Of course many other types of recursive filters may be used as well.

In one embodiment, the recursive filter 52 may be a Kalman filter (hereinafter references to a "Kalman filter" also apply to an "Extended Kalman filter") which is configured to process the measured glucose results 40 (i.e., the raw glucose sensor data) in a second-order linear system, as embodied in the equations below. The Kalman filter may comprise inter alia a state vector which represents the estimated state of the variable being estimated, which in this example is the glucose level of the person. The Kalman filter may include a prediction step, in which an a priori state and covariance are predicted, as wells as a measurement step, in which the a posteriori Kalman gain ($K_k$), the state vector, and the covariance is updated. The state vector may be updated every time a new input is received (i.e., recursively). In this disclosure, the variables in the state vector x may represent an estimate of the person's actual glucose level, based on the measured glucose results 40. The estimated glucose level vector, x, may represent the estimated glucose level of the person, g; its first derivative, ġ; and its second derivative, g̈. The measured glucose results vector, z, may include the current CG and ΔCG values. Other dynamic models may be used as well. The vectors x and z may be represented as $x_k=[g\ \dot{g}\ \ddot{g}]^T$ and $z_k=[CG\ \Delta CG]^T$, where k represents kth sample. The following equation may be used to estimate the glucose level vector, x: $x_k=\hat{x}_k+K_k(z_k-H\hat{x}_k)$ $Q_{total}$, where k represents the kth sample, $\hat{x}_k=Ax_{k-1}$, $K_k$ is the Kalman gain, and the total quality score $Q_{total}$ 61. In this fashion, the total quality score $Q_{total}$ 61 resulting from $P_A$ 58 that is based on the measured glucose results 40 and $Q_{AC}$ 59, that is based on the corresponding AC impedance measurements 41, may be used to weight the measured glucose results 40, embodied in the matrix $z_k$. The matrices and supporting equations for the Kalman filter may be as follows:

$$A = \begin{bmatrix} 1 & 1 & 0 \\ 0 & \beta_1 & 1 \\ 0 & 0 & \beta_2 \end{bmatrix}, Q = \begin{bmatrix} \sigma_g^2 & 0 & 0 \\ 0 & \sigma_{\dot{g}}^2 & 0 \\ 0 & 0 & \sigma_{\ddot{g}}^2 \end{bmatrix}, H = \begin{bmatrix} 1 & 0 & 0 \\ 0 & 1 & 0 \end{bmatrix},$$

$$\hat{P}_k = AP_{k-1}A^T + Q_{k-1},$$

$$K_k = \hat{P}_k H^T (H\hat{P}_k H^T + R_k)^{-1},$$

$$P_k = (I - K_k H)\hat{P}_k,$$

$$R_k = \max[\min((\sigma_{z-x}^2)^\alpha, \sigma_{max}^2), (1 - Q_{total})\sigma_{max}^2] + \sigma_{cgm}^2$$

$$C_{k-i} = CG_{k-i} - Hx_{k-1}, \text{ and}$$

$$\bar{C} = \frac{1}{\tau}\sum_{i=1}^{\tau} C_{k-i}.$$

It is to be appreciated that parameter $\sigma_{z-x}^2$ is the standard deviation of the difference between raw measurements (z) of the glucose sensor 16 and filtered measurements (x) of the glucose sensor 16 over the last sampling period, e.g., last 10 minutes, collected by the CGM system 10. In addition, parameter $\sigma_{cgm}^2$ is the minimum variance for CGM collected data. As the glucose sensor 47 never has zero uncertainty, the parameter $\sigma_{cgm}^2$ ensures that there is always a minimum amount of uncertainty.

The parameters $\beta_1$ and $\beta_2$ in matrix A may be set to slightly less than one (1) so that the estimated glucose level is damped when sensor malfunction occurs. The matrix Q may represent the process noise covariance, while $K_k$ may represent the Kalman filter gain that uses the estimated $R_k$ based on $Q_{total}$ 61 to provide a probability based controller gain. Additionally, the output of the filter, i.e., the estimated $R_k$ based on $Q_{total}$ 61, may also be used as input to the algorithms described in commonly owned U.S. patent application Ser. Nos. 14/677,148 and 14/229,016, the disclosures of which are herein incorporated fully by reference. Each of these algorithms uses the estimate of uncertainty provided by the Kalman filter, and thus would be impacted by an improved estimation of sensor uncertainty. Initial estimates for these parameters may be determined as is known in the art.

In the Extended Kalman filter (EKF), the system may be represented with a nonlinear model, $\hat{x}_k=f(x_{k-},u_k)$, and measurements are also represented with a nonlinear model, $z_k=h(x_k)$. This nonlinear model may include inputs from other sources, $u_k$, that may include meals, insulin, exercise or other inputs that may affect the glucose model. The nonlinear model may be derived from proprietary glucose physiological models. The prediction step is done by evaluating the nonlinear model, and the predicted uncertainty is calculated using the Jacobian of the model, $F_k$, with the state vector. This creates a localized linear model about the current system state. It is to be appreciated that $H_k$ is the mapping between the Kalman filter state (x) and the measurements (z), in which the filter state (x) includes at least the glucose, rate-of-change and acceleration, whereas the measurement vector (z) only includes glucose and rate-of-change. The following equations may be used by the EKF:

$$F_k = \begin{bmatrix} \frac{\partial f_1}{\partial x_1} & \cdots & \frac{\partial f_1}{\partial x_N} \\ \vdots & \ddots & \vdots \\ \frac{\partial f_N}{\partial x_1} & \cdots & \frac{\partial f_N}{\partial x_N} \end{bmatrix}$$

-continued $$H_k = \begin{bmatrix} \frac{\partial h_1}{\partial x_1} & \cdots & \frac{\partial h_1}{\partial x_N} \\ \vdots & \ddots & \vdots \\ \frac{\partial h_M}{\partial x_1} & \cdots & \frac{\partial h_M}{\partial x_N} \end{bmatrix}$$

$$\hat{x}_k = f(x_{k-1}, u_k)$$

$$\hat{P}_k = F_k P_{k-1} F_k^T + Q_{k-1}$$

$$K_k = \hat{P}_k H_k^T (H_k \hat{P}_k H_k^T + R_k)^{-1}$$

$$P_k = (I - K_k H_k) \hat{P}_k$$

$$x_k = \hat{x}_k + K_k (z_k - h(\hat{x}_k)) Q_{total}.$$

After the prediction step, the current glucose sensor measurement $CG_k$ may be used in the correction step. For example, the Kalman filter may be configured to weight the current measured glucose result with the probability of the controller gain. For example, when $Q_{total}$ 61 is low, the impact of the current measured glucose result on the Kalman filter may approach zero; conversely, when $Q_{total}$ 61 is high, the impact of the current measured glucose result may be higher. Using $Q_{total}$ 61 in this fashion may be a logical modification to the operation of the Kalman filter because, when sensor malfunction occurs, in the presence of significant noise or when the sensor is not properly contacting the PWD 11, the current measured glucose results likely provide little or no useful information regarding the actual glucose level of the person.

Distinguishing between sensor malfunction, sensor noise and sensing quality may facilitate estimating the glucose level of the person, and, as such, the Kalman filter may treat them differently. For normally distributed sensor noise or reduced sensing quality due to poor sensing placement or contact with the PWD 11, the Kalman filter may be configured to average out such noise and reduced sensing quality. This may be due to the fact that sensor noise/quality may be characterized for each type and/or batch of glucose sensors, including but not limited to the frequency range of the noise and the corresponding range of impedance/amplitude changes in the measured glucose results. These noise and quality characteristics may be embodied in some or all of the parameters of the Kalman filter (e.g., in $\sigma_{max}^2$ $\sigma_{cgm}^2$) such that the Kalman filter is configured to filter out the noise and poorly sensed values, and provide a relatively accurate estimated glucose level of the person, even in the presence of the sensor noise and/or poor sensing quality. On the other hand, sensor malfunction error is generally not normally distributed, so it should be handled differently within the Kalman filter framework. In one embodiment of the Kalman filter, $Q_{total}$ 61 (determined by the probability analysis tool) may be used by the Kalman filter to weight the measured glucose results such that, when sensor malfunction occurs or when the sensor quality is poor due to contact/placement issues indicated in the corresponding impendence data 41, the measured glucose results 40 are largely ignored.

An example of the operation of a Kalman filter is shown in FIG. 6, which depicts the measured glucose results 40 and the output from recursive filter 52, i.e., an estimated glucose level 60 of the person. Normally, the person's estimated glucose level 60 may generally follow the measured glucose results 40. However, during time period 70, the sensor may malfunction; at the same time, the total quality score $Q_{total}$ 61 may decrease to near 0% (as determined by the operation of the probability analysis tool 54) so as to account for a low probability of glucose sensor accuracy in the control gain. Accordingly, the Kalman filter may take into account the total quality score $Q_{total}$ 61, due to a low $P_A$ 58, so as to lessen the importance of the measured glucose results in estimating the glucose level of the person during the time period 70 of the sensor malfunction.

Continuing to refer to FIG. 6, the measured glucose results 40 may contain noise and/or a period of poor sensing quality during time period 72. The Kalman filter may filter this noise and/or poor sensing quality so as to produce an estimated glucose level 60 which is relatively smooth during this time period 72. Although the measured glucose results may contain noise and/or poor sensing quality during time period 72, the total quality score $Q_{total}$ 61, based on a high $P_A$ 58 or $Q_{ac}$ 59, may remain relatively high (e.g., near 100%) during this time since the probability analysis tool may be able to discern between sensor noise/sensing quality and sensor malfunction. As such, the Kalman filter may continue to place a relatively high importance on the measured glucose results during time period 72 (as evidenced by the total quality score $Q_{total}$ 61 being relatively high during time period 72).

The glucose sensor measurement uncertainty, $R_k$, is generally not constant. It may currently be estimated as a function of recent sensor measurements, z; the total quality score $Q_{total}$ 61; the maximum uncertainty of the measurement, $\sigma_{max}^2$; and the normal uncertainty associated with continuous glucose measurements, $\sigma_{cgm}^2$. Parameter $\sigma_{max}$ may be calculated as the maximum physiological variance for glucose in a person with poorly controlled diabetes. It may be estimated from samples of CGM data. Similarly, parameter $\sigma_{cgm}$ is the minimal uncertainty for a glucose sensor when working properly. It may be the best case performance for a sensor and may be estimated by the variance of the measured glucose results compared to fingerstick data when the sensor is performing ideally. There may be other methods for estimating the measurement uncertainty that include using higher frequency glucose sensor data. This may be interpreted as the variance of the difference between recent past CG measurements and the estimated Kalman filter state.

The estimated glucose level of the person, as determined by the recursive filter, may be used to predict the glucose level of the person at some time in the future. These estimates may also be used to analyze the person's behavior and glucose patterns. Referring back to FIG. 4, a prediction algorithm 62 may be used to predict whether and/or when the person may become hypoglycemic and may provide associated alarms or warnings. The prediction algorithm 62 may receive the person's estimated glucose level 60 from the recursive filter 52 and may also receive the uncertainty of the estimated glucose level. However, the prediction algorithm 62 may be augmented with other input data, including meal times, carbohydrates, medications, exercise, insulin doses, and so forth. The prediction algorithm 62 may further receive information from other sources of data as well such as the measured glucose results (i.e., the raw glucose sensor data) or processed glucose sensor data. The prediction algorithm 62 may use Gaussian Process regression to learn a patient specific prediction model, indicated by the training model 64 in FIG. 4. The prediction algorithm 62 may also estimate the uncertainty of the prediction, which may allow the alarm thresholds to be adjusted for sensitivity. The alarm thresholds may also be adjusted based on the person's current activity; for example, the sensitivity could be increased when the person is sleeping.

As an example, the prediction of hypoglycemia can be done using the system model of the Kalman filter or the Extended Kalman filter. In this example the prediction step, $\hat{x}_k = Ax_{k-1}$ or $\hat{x}_k = f(x_{k-1}, u_k)$, is iterated for the desired prediction time and the predicted value is compared to the specific threshold. For example, if Kalman filter is updated every one minute, the prediction step may iterate the Kalman filter forty-five times in order to predict the glucose level of the person from the present to forty-five minutes in the future. The prediction model may include additional predicted inputs such as anticipated meals, insulin, exercise, or other anticipated future inputs.

In another example, the estimated glucose value, g, and rate-of-change of the glucose value, ġ, as estimated by the recursive filter are used to define a linear forecast which is compared to the hypoglycemia threshold. The forecast is done with the following equation by multiplying the derivative by the desired prediction time, $t_{pr}$, to calculate the predicted glucose value, ĝ.

$$\hat{g} = g + \dot{g} t_{pr}.$$

As an example, the specific input vectors used may include three samples of the estimated glucose levels (CG) taken at time t=0, −15, and −30 minutes, the current derivative of the estimated glucose level and the derivative at t=−15 minutes, and the time since the last meal. The meal information, $t_{meal}$, and bolus information, B, are optional and other data can also be included. This may be expressed mathematically as $$x_{CG} = [CG_{t=0}\ CG_{t=-15}\ CG_{t=-30}\ \Delta CG_{t=0} \ldots\ _{-15} \Delta CG_{t=-15} \ldots\ _{-}]^T$$

$$x_{meal} = [CG_{t=0}\ CG_{t=-15}\ CG_{t=-30}\ \Delta CG_{t=0} \ldots\ _{-15} \Delta CG_{t=-15} \ldots\ _{-30} \min(t_{meal}, t_{max})\ B]^T$$

Gaussian process regression may use the following equation to predict future glucose levels of the person based on training data, represented by (X,y), and the test point (x*, y*):

$$y^* = k(x^*, X)(k(X, X) + \mu I)^{-1} y,$$

where k(x,x) is a covariance function. A Gaussian covariance function may be used to generate the results, but other functions can be used here as well. A Gaussian covariance function which may be used is:

$$k(\hat{x}, x) = \exp\left[-\frac{1}{2\sigma_k^2} \|\hat{x} - x\|^2\right].$$

Figure 7:
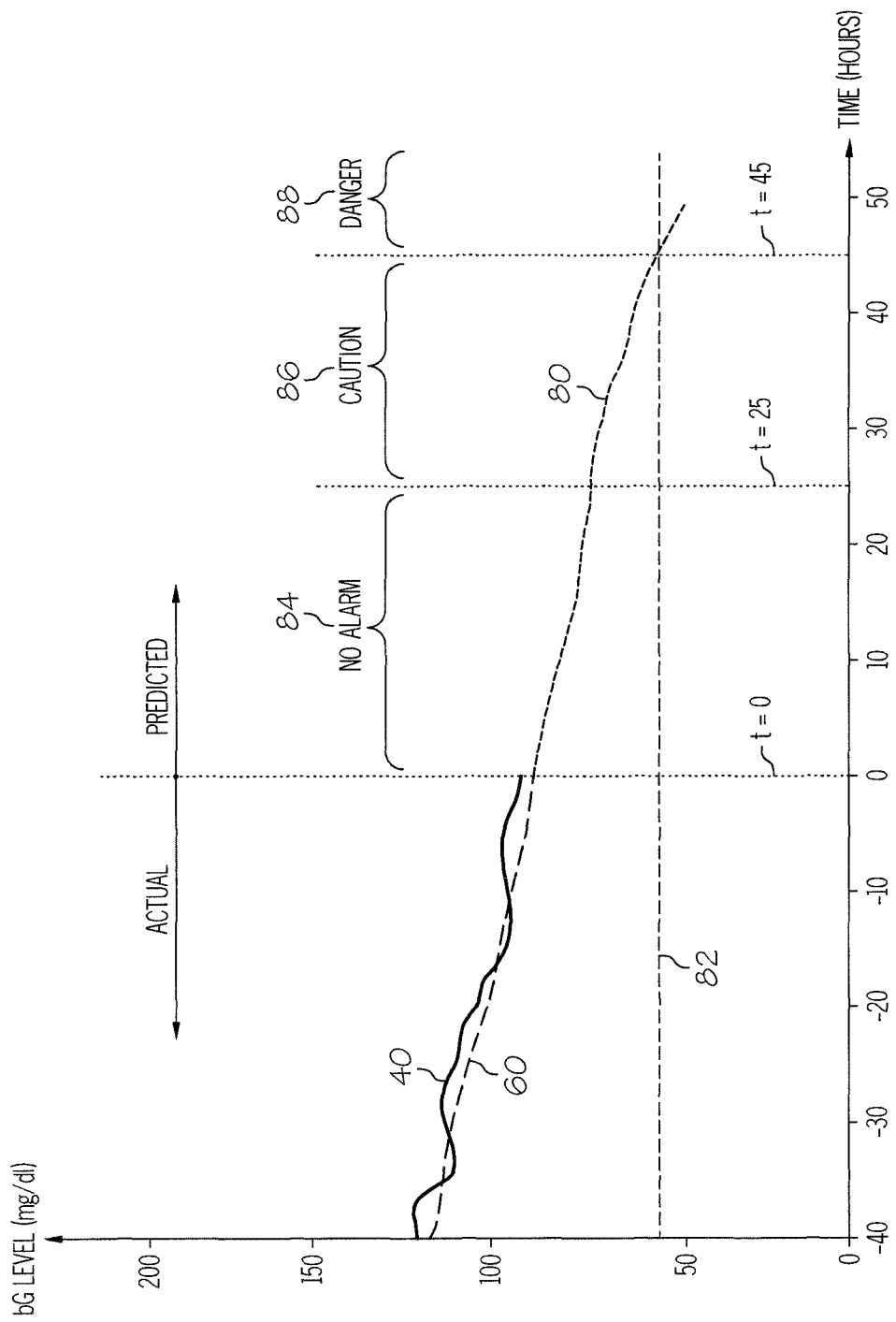
FIG. 7 depicts the operation of a prediction algorithm according to one or more embodiments shown and described herein.

FIG. 7 depicts the operation of the prediction algorithm. The measured glucose results 40 from the glucose sensor, and the estimated glucose level 60 of the person (i.e., the output of the Kalman filter) are shown on the left (from a time t=−40 to 0). The current time is t=0, The prediction algorithm may determine the person's predicted glucose level 80 at some time in the future (i.e., any time greater than t=0). Furthermore, the prediction algorithm may be used to predict whether and/or when the glucose level of the person may become hypoglycemic. A hypoglycemic threshold 82 may be established for the person, such that an actual glucose level below this threshold means the person has become hypoglycemic. The hypoglycemic threshold 82 may be uniquely determined for each person. The threshold for an average person may be about 50 mg/ml. Also the hypoglycemic threshold 82 may vary for each person, such that the threshold is based on time, on an event, or combinations thereof. As examples, the hypoglycemic threshold 82 for a person may depend on the time of day, whether the person has taken medication, whether and/or how long the glucose sensor is in the dropout state, and so forth. The prediction algorithm may be able to predict when the person may become hypoglycemic. In FIG. 7, the prediction algorithm may predict that the person will become hypoglycemic at t=45 (i.e., 45 minutes from the current time). Of course, as time progresses, the prediction algorithm may continue to use the latest estimated glucose level (from the Kalman filter) and adjust the predicted glucose levels accordingly.

In addition to being able to predict future values of the glucose level of the person, the prediction algorithm may be further configured to determine the probability that the prediction is accurate. For example, predictions only one or two minutes in the future may be highly accurate, while predictions which are 60 or 70 minutes in the future may be relatively inaccurate. Of course the probability that the prediction is accurate may be a continuum, starting at near 100% for the immediate future and decaying to near 0% as the prediction reaches further into the future. This information may be used, in conjunction with the actual prediction itself, to provide a hypoglycemia warning system for the person. As shown in FIG. 7, the warning system may provide no alarm 84 when the predicted glucose level 80 is sufficient high above the hypoglycemic threshold 82; it may advise caution 86 when the predicted glucose level 80 approaches within a predetermined range of the hypoglycemic threshold 82; and it may advise danger 88 when the predicted glucose level 80 drops below the hypoglycemic threshold 82.

The prediction algorithm, as previously discussed, may include a training function which learns the specific characteristics of a person. The training function may produce training data which may be used in the prediction algorithm and may be weighted based on the influence they have on generating the prediction. The level of influence the training data may be determined by the covariance function k(x,x) used within the Gaussian Process regressor.

The prediction algorithm may be initialized with a generic set of training examples or no training examples. As new data are measured they may be incorporated into the prediction algorithm and/or training function. There are many possible algorithms for including new data. These include adding the data to the training set when 1) A predetermined period of time has elapsed, 2) The prediction failed on the specific data, 3) The input data is not represented in the training set, or 4) A patient or care provider manually includes the data, including all new data, if suitable.

When added to the training set, the new data can be included as a new vector, or by reweighing an existing training vector. The second method includes the benefit of maintaining constant memory needs. After adding additional data, the prediction algorithm may be updated immediately on the device, retrospectively on a personal computer, or retrospectively at a clinic.

Figure 8:
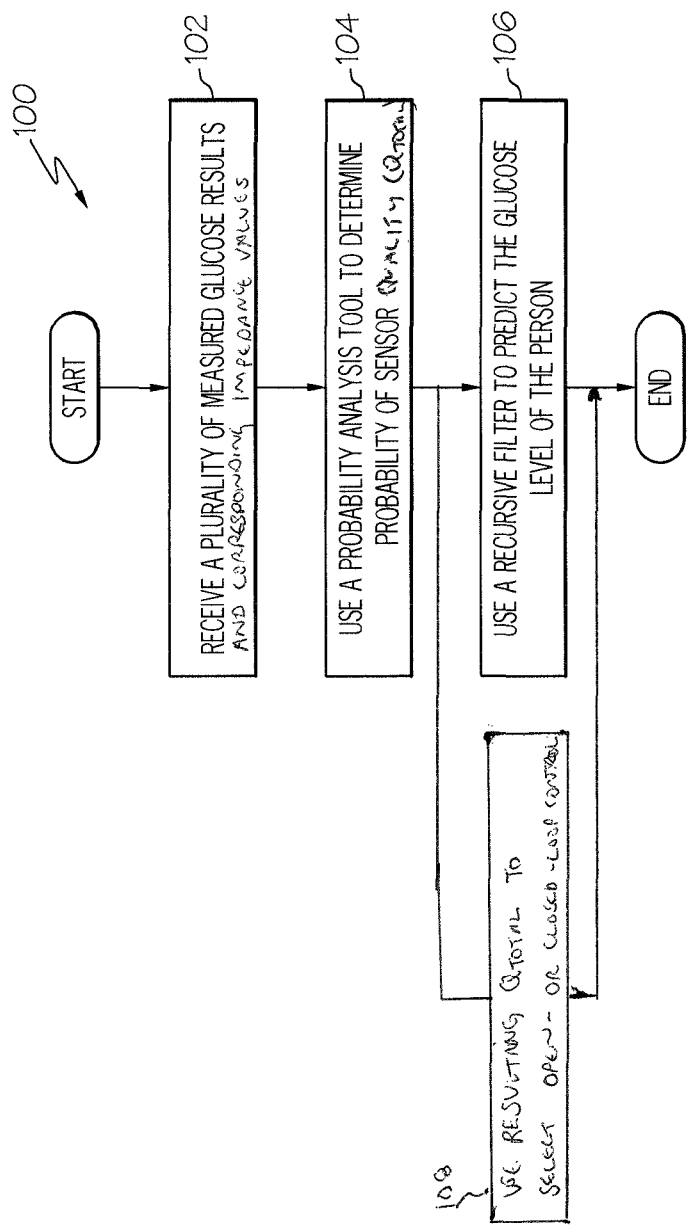
FIG. 8 depicts a method of predicting the glucose level of the person and selecting automatically open-loop and closed-loop control for a connected therapy delivery device using a probability analysis tool and a recursive filter according to one or more embodiments shown and described herein.

Referring to FIGS. 4 and 8, a method 100 is shown for estimating a glucose level of a person having diabetes as well as selecting either open- or closed-loop control for a connected therapy delivery device 31. By the term "connected" it is meant either wired or wireless connected as know in the art. The method 100 may comprise a number of acts, which may be performed in any suitable order. In FIG. 8, at act 102, the method 100 may receive into the blood glucose management device 26 a plurality of measured glucose results 40 and corresponding impedance values 41 from the glucose sensor 16 coupled to the person. At act 104, the method 100 may use the blood glucose management device 26 to analyze the plurality of measured glucose results 40 and corresponding impedance values 41 with a probability analysis tool 54 configured to determine a probability of sensor quality, i.e., a total quality score $Q_{total}$ 61 from a set of computed quality metrics based on such received measured glucose results 40 and associated impedance data 41. At act 106, the method 100 may use the blood glucose management device 26 to estimate a glucose level of the person using a recursive filter configured to weight the plurality of measured glucose results with the total quality score $Q_{total}$ 61. In addition, at act 108, the method 100 may use the blood glucose management device 26 to select either open-loop glucose control 45 or closed-loop glucose control 47 in which to operate the therapy deliver device 31 based on the resulting total quality score $Q_{total}$ 61. The probability analysis tool and the recursive filter may be established as described hereinabove.

It should now be understood that the methods and systems described herein may be used to estimate the glucose level of a person having diabetes, even in the presence of noise and/or sensor inaccuracy (e.g., sensor dropout), as well as to select automatically which mode of operation (open- or closed-loop) the microcontroller 32 will operate the therapy delivery device 31 during a given period based on routinely received measured glucose results 40 and associated impedance data 41. Furthermore, the methods and systems described herein may also be used to predict the future glucose level of the person. As such, they may be able to predict whether and/or when the person's glucose level may become hypoglycemic. Upon detecting or predicting that the person may become hypoglycemic, the methods and systems may provide corresponding information to the person, such as for example a warning. The methods described herein may be stored on a computer-readable medium which has computer-executable instructions for performing the methods. Such computer-readable media may include compact discs, hard drives, thumb drives, random-access memory, dynamic random-access memory, flash memory, and so forth.

It is noted that recitations herein of a component of the present disclosure being "configured" in a particular way, "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A method for estimating glucose level of a person having diabetes and selecting automatically open-loop and closed-loop control for a connected therapy delivery device, the method comprising:
   receiving into a blood glucose management device having a microcontroller a plurality of measured glucose results and corresponding impedance values from a glucose sensor coupled to the person;
   using the microcontroller to analyze the plurality of measured glucose results and corresponding impedance values with a probability analysis tool configured to determine a total quality score $Q_{total}$ that is based on the minimum constraint of a set of quality metrics which comprises a probability of glucose sensor accuracy $P_A$ based on the plurality of measured glucose results and a probability of sensing quality $Q_{ac}$ based on the impedance values;
   using the microcontroller to estimate the glucose level of the person with a recursive filter configured to estimate the glucose level based on the plurality of measured glucose results weighted with the total quality score $Q_{total}$; and
   switching, via the microcontroller, the connected therapy delivery device automatically between open-loop control and closed-loop control based on the value of the total quality score $Q_{total}$.

2. The method of claim 1, wherein the blood glucose management device comprises a blood glucose meter, and the microcontroller is coupled to the glucose sensor, a cellular phone, a smart phone, a personal digital assistant, a personal computer, or a computer server.

3. The method of claim 1, wherein the glucose sensor comprises a continuous glucose monitoring system physically coupled to the person having diabetes and configured to automatically measure the glucose level of the person, and the connected therapy delivery device is an infusion pump, wherein the infusion pump is wired or wireless connected to the blood glucose management device.

4. The method of claim 1, wherein the plurality of measured glucose results comprises periodic glucose measurements taken in period selected from the range of every 1 to 10 minutes.

5. The method of claim 1, wherein the probability analysis tool is configured to determine the total quality score $Q_{total}$ further based on at least one of:
   when the person eats a meal;
   when the person exercises; and
   when insulin is delivered to the person.

6. The method of claim 1, wherein the probability analysis tool comprises a hidden Markov model, wherein:
   the hidden Markov model has two states:
      a first state $S_A$ indicating the glucose sensor is accurate, and
      a second state $S_I$ indicating the glucose sensor is inaccurate; and
   the hidden Markov model is configured to determine the probability of glucose sensor accuracy $P_A$, based on a state of the hidden Markov model and the plurality of measured glucose results.

7. The method of claim 6, wherein probability of the glucose sensor being in the second state $S_I$ is based on a most-recent measured glucose result, a most-recent change in the plurality of measured glucose results, or a combination thereof.

8. The method of claim 6, wherein probability of the hidden Markov model transitioning from the first state $S_A$ to second the state $S_I$ is $$P_{A \to I} = \min\left[\left(1 - \frac{1}{1 + e^{-(\Delta CG + \alpha_1/\alpha_2)}}\right) + \left(1 - \frac{1}{1 + e^{-(CG + \alpha_3/\alpha_4)}}\right), 1\right],$$

where CG is a most-recent measured glucose result, $\Delta$CG is a most-recent change in the plurality of measured glucose results, and $\alpha_1, \alpha_2, \alpha_3$, and $\alpha_4$ are constants related to characteristics of the glucose sensor.

9. The method of claim 6, wherein probability of the hidden Markov model remaining in the second state $S_I$ is $$P_{I \to I} = \max\left[\gamma P_{I_{k-1}} - \left(\frac{1}{1 + e^{-(\Delta CG + \alpha_5)/\alpha_6}}\right), 0\right],$$

where ΔCG is a most-recent change in the plurality of measured glucose results, $P_{I_{k-1}}$ is a previous probability of transitioning to or being in the second state $S_I$, and $\gamma$, $\alpha_5$, and $\alpha_6$ are constants related to characteristics of the glucose sensor.

10. The method of claim 6, wherein the probability of glucose sensor accuracy $P_A$ is $1 - [(P_{A \to I} \times S_A) + (P_{I \to I} \times S_I)]$, wherein $S_A = 1$ when the hidden Markov model is in the first state $S_A$ and $S_A = 0$ otherwise, $S_I = 1$ when the hidden Markov model is in the second state $S_I$ and $S_I = 0$ otherwise, $P_{A \to I}$ is a probability of transitioning from the first state $S_A$ to the second state $S_I$, and $P_{I \to I}$ is a probability of remaining in the second state $S_I$ when in the second state $S_I$.

11. The method of claim 1, wherein the recursive filter is a Kalman filter or an Extended Kalman filter.

12. The method of claim 11 further comprising using the microcontroller to predict a future glucose level of the person with the Kalman filter or the Extended Kalman filter, wherein:

the Kalman filter or the Extended Kalman filter comprises a prediction step and a measurement step; and the prediction step is performed one or more times in order to predict the future glucose level of the person.

13. The method of claim 11, wherein the Kalman filter or the Extended Kalman filter comprises a state vector, $x_k = [g \ \dot{g} \ \ddot{g}]^T$, where k represents a kth sample of the state vector, g represents the estimated glucose level of the person, $\dot{g}$ represents a first derivative of g, and $\ddot{g}$ resents a second derivative of g.

14. The method of claim 13, wherein using the microcontroller to estimate the glucose level of the person comprises determining the state vector $x_k = \hat{x}_k + K_k(z_k - h(\hat{x}_k))Q_{total}$, where $\hat{x}$ $$\hat{x}_k = \begin{bmatrix} 1 & 1 & 0 \\ 0 & \beta_1 & 1 \\ 0 & 0 & \beta_2 \end{bmatrix} x_{k-1}, z_k = [CG \ \Delta CG]^T, H = \begin{bmatrix} 1 & 0 & 0 \\ 0 & 1 & 0 \end{bmatrix},$$

CG is a most-recent measured glucose result at time k, ΔCG is a most-recent change in the plurality of measured glucose results, $K_k$ is a Kalman gain, $Q_{total}$ is the total quality score, and $\beta_1$ and $\beta_2$ are constants related to characteristics of the glucose sensor.

15. The method of claim 14, wherein the Kalman gain $K_k$ is based on a measurement uncertainty $R_k$ such that the measurement uncertainty $R_k$ is variable and is based on the probability of sensor accuracy.

16. The method of claim 15, wherein the measurement uncertainty $R_k$ is:

$R_k = \max[\min((\sigma_{z-x}^2)^\alpha, \sigma_{max}^2 (1-Q_{total})\sigma_{max}^2] + \sigma_{cgm}^2$, where $(\sigma_{z-x}^2)^\alpha$, represents is the standard deviation of the difference between raw CGM measurements (z) and filtered CGM measurements (x) over a last sampling period, $\sigma_{max}^2$ represents a maximum physiological variance for glucose in a person with poorly controlled diabetes, $Q_{total}$ is the total quality score, and $\sigma_{cgm}^2$ represents a minimum variance for the raw CGM measurements.

17. The method of claim 16, wherein the recursive filter is configured to estimate the glucose level of the person further based on at least one of:

when the person eats a meal;

when the person exercises; and when insulin is delivered to the person.

18. The method of claim 1 further comprising using the microcontroller to predict a future glucose level of the person with a regression analysis tool configured to predict the future glucose level based on the estimated glucose level of the person from the recursive filter.

19. The method of claim 18, wherein the regression analysis tool comprises a Gaussian process regression analysis.

20. The method of claim 19, wherein the Gaussian process regression analysis comprises a training algorithm configured to learn one or more characteristics of the person related to the glucose level of the person.

21. An apparatus for estimating a glucose level of a person having diabetes and selecting automatically open-loop and closed-loop control for a connected therapy delivery device, the apparatus comprising a microcontroller and a display, wherein:

the microcontroller is configured to:

receive a plurality of measured glucose results and corresponding impedance values from a glucose sensor coupled to the person, analyze the plurality of measured glucose results and corresponding impedance values with a probability analysis tool configured to determine a total quality score $Q_{total}$ that is based on the minimum constraint of a set of quality metrics which comprises a probability of glucose sensor accuracy $P_A$ based on the plurality of measured glucose results and a probability of sensing quality $Q_{ac}$ based on the impedance values, estimate the glucose level of the person with a recursive filter configured to estimate the glucose level based on the plurality of measured glucose results weighted with the total quality score $Q_{total}$, switch the connected therapy delivery device automatically between open-loop control and closed-loop control based on the value of the total quality score $Q_{total}$, and transmit to the display information related to the estimate of the glucose level of the person and the control switch of the therapy delivery device.

22. The apparatus of claim 21, wherein the microcontroller is coupled to the glucose sensor, a cellular phone, a smart phone, a personal digital assistant, a personal computer, or a computer server.

23. The apparatus of claim 21, wherein the glucose sensor comprises a continuous glucose monitoring system physically coupled to the person having diabetes and configured to automatically measure the glucose level of the person, and the connected therapy delivery device is a infusion pump, wherein the infusion pump is wired or wireless connected to the blood glucose management device.

24. The apparatus of claim 21, wherein the plurality of measured glucose results comprises periodic glucose measurements taken in period selected from the range of every 1, 5 or 10 minutes.

25. The apparatus of claim 21, wherein the probability analysis tool is configured to determine the total quality score $Q_{total}$ further based on at least one of:
when the person eats a meal;
when the person exercises; and
when insulin is delivered to the person.

26. The apparatus of claim 21, wherein the probability analysis tool comprises a hidden Markov model, wherein:
the hidden Markov model has two states:
a first state $S_A$ indicating the glucose sensor is accurate, and
a second state $S_I$ indicating the glucose sensor is inaccurate; and
the hidden Markov model is configured to determine the probability of glucose sensor accuracy $P_A$, based on a state of the hidden Markov model and the plurality of measured glucose results.

27. The apparatus of claim 26, wherein probability of the glucose sensor being in the second state $S_I$ is based on a most-recent measured glucose result, a most-recent change in the plurality of measured glucose results, or a combination thereof.

28. The apparatus of claim 26, wherein probability of the hidden Markov model transitioning from the first state $S_A$ to second the state $S_I$ is $$P_{A \to I} = \min\left[\left(1 - \frac{1}{1+e^{-(\Delta CG+\alpha_1/\alpha_2)}}\right) + \left(1 - \frac{1}{1+e^{-(CG+\alpha_3)/\alpha_4}}\right), 1\right],$$

where CG is a most-recent measured glucose result, $\Delta CG$ is a most-recent change in the plurality of measured glucose results, and $\alpha_1$, $\alpha_2$, $\alpha_3$, and $\alpha_4$ are constants related to characteristics of the glucose sensor.

29. The apparatus of claim 26, wherein probability of the hidden Markov model remaining in the second state $S_I$ is $$P_{I \to I} = \max\left[\gamma P_{I_{k-1}} - \left(\frac{1}{1+e^{-(\Delta CG+\alpha_5)/\alpha_6}}\right), 0\right],$$

where $\Delta CG$ is a most-recent change in the plurality of measured glucose results, $P_{I_{k-1}}$ is a previous probability of transitioning to or being in the second state $S_I$, and $\gamma$, $\alpha_5$, and $\alpha_6$ are constants related to characteristics of the glucose sensor.

30. The apparatus of claim 26, wherein the probability of glucose sensor accuracy $P_A$ is $1-[(P_{A \to I} \times S_A)+(P_{I \to I} \times S_I)]$, wherein $S_A=1$ when the hidden Markov model is in the first state $S_A$ and $S_A=0$ otherwise,
$S_I=1$ when the hidden Markov model is in the second state $S_I$ and $S_I=0$ otherwise,
$P_{A \to I}$ is a probability of transitioning from the first state $S_A$ to the second state $S_I$, and
$P_{I \to I}$ is a probability of remaining in the second state $S_I$ when in the second state $S_I$.

31. The apparatus of claim 21, wherein the recursive filter is a Kalman filter or an Extended Kalman filter.

32. The apparatus of claim 31, wherein the microcontroller predicts a future glucose level of the person with the Kalman filter or the Extended Kalman filter, wherein:
the Kalman filter or the Extended Kalman filter comprises a prediction step and a measurement step; and
the prediction step is performed one or more times in order to predict the future glucose level of the person.

33. The apparatus of claim 31, wherein the Kalman filter or the Extended Kalman filter comprises a state vector, $x_k=[g\ \dot{g}\ \ddot{g}]^T$, where k represents a kth sample of the state vector, g represents the estimated glucose level of the person, $\dot{g}$ represents a first derivative of g, and $\ddot{g}$ represents a second derivative of g.

34. The apparatus of claim 33, wherein the microcontroller estimates the glucose level of the person via state vector $x_k = \hat{x}_k + K_k(z_k - h(\hat{x}_k))Q_{total}$, where $$\hat{x}_k = \begin{bmatrix} 1 & 1 & 0 \\ 0 & \beta_1 & 1 \\ 0 & 0 & \beta_2 \end{bmatrix} x_{k-1},\ z_k = [CG\ \Delta CG]^T,\ H = \begin{bmatrix} 1 & 0 & 0 \\ 0 & 1 & 0 \end{bmatrix},$$

CG is a most-recent measured glucose result, $\Delta CG$ is a most-recent change in the plurality of measured glucose results, $K_k$ is a Kalman gain, $Q_{total}$ is the total quality score, and $\beta_1$ and $\beta_2$ are constants related to characteristics of the glucose sensor.

35. The apparatus of claim 34, wherein the Kalman gain $K_k$ is based on a measurement uncertainty $R_k$ such that the measurement uncertainty $R_k$ is variable and is based on the probability of sensor accuracy.

36. The apparatus of claim 35, wherein the measurement uncertainty $R_k$ is:

$R_k = \max[\min((\sigma_{z-x}^2)^\alpha, \sigma_{max}^2), (1-Q_{total})\sigma_{max}^2] + \sigma_{cgm}^2$, where $\sigma_{z-x}^2)^\alpha$, represents is the standard deviation of the difference between raw CGM measurements (z) and filtered CGM measurements (x) over a last sampling period, $\sigma_{max}^2$ represents a maximum physiological variance for glucose in a person with poorly controlled diabetes, $Q_{total}$ is the total quality score, and $\sigma_{cgm}^2$ represents a minimum variance for the raw CGM measurements.

37. The apparatus of claim 36, wherein the recursive filter is configured to estimate the glucose level of the person further based on at least one of:
when the person eats a meal;
when the person exercises; and
when insulin is delivered to the person.

38. The apparatus of claim 21, wherein the microcontroller predicts a future glucose level of the person with a regression analysis tool configured to predict the future glucose level based on the estimated glucose level of the person from the recursive filter.

39. The apparatus of claim 38, wherein the regression analysis tool comprises a Gaussian process regression analysis.

40. The apparatus of claim 39, wherein the Gaussian process regression analysis comprises a training algorithm configured to learn one or more characteristics of the person related to the glucose level of the person.

41. A method for estimating glucose level of a person having diabetes, the method comprising:

collecting, via a blood glucose management device having a microcontroller, a plurality of measured glucose results and corresponding impedance values from a glucose sensor coupled to the person;

using the microcontroller to analyze the plurality of measured glucose results and corresponding impedance values with a probability analysis tool configured to determine a total quality score $Q_{total}$ that is based on the minimum constraint of a set of quality metrics which comprises a probability of glucose sensor accuracy $P_A$ based on the plurality of measured glucose results and a probability of sensing quality $Q_{ac}$ based on the impedance values;

using the microcontroller to estimate the glucose level of the person with a recursive filter configured to estimate the glucose level based on the plurality of measured glucose results weighted with the total quality score $Q_{total}$; and alerting via the microcontroller updating a display of the management device with a warning upon the estimated glucose level of the person being one of hypoglycemic and hyperglycemic.

42. An apparatus for estimating a glucose level of a person having diabetes, the apparatus comprising a microcontroller and a display, wherein:

the microcontroller is configured to:

collect a plurality of measured glucose results and corresponding impedance values from a glucose sensor coupled to the person, analyze the plurality of measured glucose results and corresponding impedance values with a probability analysis tool configured to determine a total quality score $Q_{total}$ that is based on the minimum constraint of a set of quality metrics which comprises a probability of glucose sensor accuracy $P_A$ based on the plurality of measured glucose results and a probability of sensing quality $Q_{ac}$ based on the impedance values, estimate the glucose level of the person with a recursive filter configured to estimate the glucose level based on the plurality of measured glucose results weighted with the total quality score $Q_{total}$, transmit to the display information related to the estimate of the glucose level of the person, and alert via the display with a warning upon the estimated glucose level of the person being one of hypoglycemic and hyperglycemic.

43. The method of claim 1 further comprises determining the probability of sensing quality $Q_{ac}$ based on the impedance values via utilizing the equation:

$$Q_{AC}=0.5*(1-\tan h(a*\log(b*E)),$$

where E is a deviation sum from predetermined values, and parameters a and b are preselected to choose a location of a 0.5 value (1/b) and a rate of change at a 0.5 value (a).

44. The apparatus of claim 21, wherein the microcontroller is configured to determine the probability of sensing quality $Q_{ac}$ based on the impedance values via the equation:

$$Q_{AC}=0.5*(1-\tan h(a*\log(b*E)),$$

where E is a deviation sum from predetermined values, and parameters a and b are preselected to choose a location of a 0.5 value (1/b) and a rate of change at a 0.5 value (a).

* * * * *

UNITED STATES PATENT AND TRADEMARK OFFICE
CERTIFICATE OF CORRECTION

PATENT NO. : 10,478,556 B2
APPLICATION NO. : 15/061202
DATED : November 19, 2019
INVENTOR(S) : Harvey B. Buck, Jr. and David L. Duke Page 1 of 1

It is certified that error appears in the above-identified patent and that said Letters Patent is hereby corrected as shown below:

In the Claims

In Column 20, Line(s) 63-64, delete
" $P_{A \to I} = \min\left[\left(1 - \frac{1}{1 + e^{-(\Delta CG + \alpha_1/\alpha_2)}}\right) + \left(1 - \frac{1}{1 + e^{-(CG + \alpha_3)/\alpha_4}}\right), 1\right],$ " and insert
-- $P_{A \to I} = \min\left[\left(1 - \frac{1}{1 + e^{-(\Delta CG + \alpha_1)/\alpha_2}}\right) + \left(1 - \frac{1}{1 + e^{-(CG + \alpha_3)/\alpha_4}}\right), 1\right],$ --, therefor.

In Column 21, Line(s) 65-67, delete
"$R_k = \max[\min((\sigma_{z-x}^2)^\alpha, \sigma_{max}^2(1-Q_{total})\sigma_{max}^2] + \sigma_{cgm}^2,$" and insert
-- $R_k = max[min((\sigma_{z-x}^2)^\alpha, \sigma_{max}^2), (1 - Q_{total})\sigma_{max}^2] + \sigma_{cgm}^2,$ --, therefor.

In Column 23, Line(s) 33-34, delete
" $P_{A \to I} = \min\left[\left(1 - \frac{1}{1 + e^{-(\Delta CG + \alpha_1/\alpha_2)}}\right) + \left(1 - \frac{1}{1 + e^{-(CG + \alpha_3)/\alpha_4}}\right), 1\right],$ " and insert
-- $P_{A \to I} = \min\left[\left(1 - \frac{1}{1 + e^{-(\Delta CG + \alpha_1)/\alpha_2}}\right) + \left(1 - \frac{1}{1 + e^{-(CG + \alpha_3)/\alpha_4}}\right), 1\right],$ --, therefor.

In Column 26, Line(s) 19-20, delete "$Q_{AC} = 0.5*(1-\tanh(a*\log(b*E)),$" and insert --$Q_{AC}=0.5*(1-\tanh(a*\log(b*E))),$--, therefor.

In Column 26, Line(s) 27-28, delete "$Q_{AC} = 0.5*(1-\tanh(a*\log(b*E)),$" and insert --$Q_{AC}=0.5*(1-\tanh(a*\log(b*E))),$--, therefor.

Signed and Sealed this
Seventh Day of April, 2020

Andrei Iancu
*Director of the United States Patent and Trademark Office*